US008900651B2

(12) United States Patent  (10) Patent No.: US 8,900,651 B2
McClain et al.  (45) Date of Patent: Dec. 2, 2014

(54) POLYMER FILMS FOR MEDICAL DEVICE COATING

(75) Inventors: James McClain, Raleigh, NC (US); Douglas Taylor, Franklinton, NC (US)

(73) Assignee: Micell Technologies, Inc., Durham, NC (US)

(*) Notice: Subject to any disclaimer, the term of this patent is extended or adjusted under 35 U.S.C. 154(b) by 155 days.

(21) Appl. No.: 12/601,101

(22) PCT Filed: Dec. 4, 2008

(86) PCT No.: PCT/US2008/064732

§ 371 (c)(1),
(2), (4) Date: Mar. 19, 2010

(87) PCT Pub. No.: WO2008/148013

PCT Pub. Date: Dec. 4, 2008

(65) Prior Publication Data

US 2010/0228348 A1    Sep. 9, 2010

Related U.S. Application Data

(60) Provisional application No. 60/940,365, filed on May 25, 2007, provisional application No. 60/979,375, filed on Oct. 11, 2007.

(51) Int. Cl.
| | |
|---|---|
| *B05D 1/06* | (2006.01) |
| *B05D 3/02* | (2006.01) |
| *B05D 1/12* | (2006.01) |
| *B05D 1/02* | (2006.01) |
| *A61L 27/34* | (2006.01) |
| *A61L 31/10* | (2006.01) |
| *B05D 1/04* | (2006.01) |
| *B05D 5/08* | (2006.01) |

(52) U.S. Cl.
CPC ............... *B05D 1/025* (2013.01); *A61L 27/34* (2013.01); *A61L 31/10* (2013.01); *B05D 1/04* (2013.01); *A61L 2420/02* (2013.01); *B05D 5/083* (2013.01); *B05D 2401/90* (2013.01)
USPC .......... 427/2.1; 427/2.24; 427/2.25; 427/180; 427/202; 427/458

(58) Field of Classification Search
USPC ......................................... 427/476, 483, 486
See application file for complete search history.

(56) References Cited

U.S. PATENT DOCUMENTS

| 3,087,660 A | 4/1963 | Endicott |
| 3,087,860 A | 4/1963 | Endicott |

(Continued)

FOREIGN PATENT DOCUMENTS

| CA | 2589761 | 12/2004 |
| CN | 1465410 | 1/2004 |

(Continued)

OTHER PUBLICATIONS

Hasegawa et al. Nylon 6/Na—montmorillonite nanocomposites prepared by compounding Nylon 6 with Na—montmorillonite slurry. Polymer. Volume 44. (2003). pp. 2933-2937.*

(Continued)

*Primary Examiner* — Cachet Sellman
(74) *Attorney, Agent, or Firm* — Wilson Sonsini Goodrich & Rosati

(57) ABSTRACT

A method for depositing a coating comprising a polymer and impermeable dispersed solid on a substrate, comprising the following steps: discharging at least one impermeable dispersed solid in dry powder form through a first orifice; discharging at least one polymer in dry powder form through a second orifice; depositing the polymer and/or impermeable dispersed solid particles onto said substrate, wherein an electrical potential is maintained between the substrate and the impermeable dispersed solid and/or polymer particles, thereby forming said coating; and sintering said coating under conditions that do not disrupt the activity and/or function of the substrate. A similar method is provided for depositing a coating comprising a hydrophobic polymer and a water-vapor-trapping material on a substrate.

25 Claims, 4 Drawing Sheets

Schematic Representing the Coating and Sintering
Process Apparatus

(56) References Cited

U.S. PATENT DOCUMENTS

| | | | |
|---|---|---|---|
| 3,123,077 A | 3/1964 | Alcamo | |
| 3,457,280 A | 7/1969 | Schmitt et al. | |
| 3,597,449 A | 8/1971 | Deprospero et al. | |
| 3,929,992 A | 12/1975 | Sehgal et al. | |
| 4,000,137 A | 12/1976 | Dvonch et al. | |
| 4,285,987 A * | 8/1981 | Ayer et al. | 427/2.16 |
| 4,326,532 A | 4/1982 | Hammar | |
| 4,582,731 A | 4/1986 | Smith | |
| 4,655,771 A | 4/1987 | Wallsten | |
| 4,733,665 A | 3/1988 | Palmaz | |
| 4,734,227 A | 3/1988 | Smith | |
| 4,734,451 A | 3/1988 | Smith | |
| 4,931,037 A | 6/1990 | Wetterman | |
| 4,950,239 A | 8/1990 | Gahara | |
| 4,985,625 A | 1/1991 | Hurst | |
| 5,000,519 A | 3/1991 | Moore | |
| 5,090,419 A | 2/1992 | Palestrant | |
| 5,096,848 A | 3/1992 | Kawamura | |
| 5,106,650 A | 4/1992 | Hoy et al. | |
| 5,158,986 A | 10/1992 | Cha et al. | |
| 5,195,969 A | 3/1993 | Wang et al. | |
| 5,243,023 A | 9/1993 | Dezern | |
| 5,270,086 A | 12/1993 | Hamlin | |
| 5,288,711 A | 2/1994 | Mitchell et al. | |
| 5,324,049 A | 6/1994 | Mistrater et al. | |
| 5,340,614 A | 8/1994 | Perman et al. | |
| 5,342,621 A | 8/1994 | Eury | |
| 5,350,361 A | 9/1994 | Tsukashima et al. | |
| 5,350,627 A | 9/1994 | Nemphos et al. | |
| 5,356,433 A | 10/1994 | Rowland et al. | |
| 5,366,504 A | 11/1994 | Andersen et al. | |
| 5,368,045 A | 11/1994 | Clement et al. | |
| 5,372,676 A * | 12/1994 | Lowe | 216/30 |
| 5,385,776 A * | 1/1995 | Maxfield et al. | 428/297.4 |
| 5,403,347 A | 4/1995 | Roby et al. | |
| 5,470,603 A | 11/1995 | Staniforth et al. | |
| 5,494,620 A | 2/1996 | Liu et al. | |
| 5,500,180 A | 3/1996 | Anderson et al. | |
| 5,556,383 A | 9/1996 | Wang et al. | |
| 5,562,922 A | 10/1996 | Lambert | |
| 5,569,463 A | 10/1996 | Helmus et al. | |
| 5,609,629 A | 3/1997 | Fearnot et al. | |
| 5,626,611 A | 5/1997 | Liu et al. | |
| 5,626,862 A | 5/1997 | Brem et al. | |
| 5,674,242 A | 10/1997 | Phan et al. | |
| 5,725,570 A | 3/1998 | Heath | |
| 5,800,511 A | 9/1998 | Mayer | |
| 5,811,032 A | 9/1998 | Kawai et al. | |
| 5,824,049 A | 10/1998 | Ragheb et al. | |
| 5,837,313 A | 11/1998 | Ding et al. | |
| 5,873,904 A | 2/1999 | Ragheb et al. | |
| 5,876,426 A | 3/1999 | Kume et al. | |
| 5,924,631 A | 7/1999 | Rodrigues et al. | |
| 5,948,020 A | 9/1999 | Yoon et al. | |
| 5,957,975 A | 9/1999 | Lafont et al. | |
| 6,013,855 A | 1/2000 | McPherson et al. | |
| 6,077,880 A | 6/2000 | Castillo et al. | |
| 6,129,755 A | 10/2000 | Mathis et al. | |
| 6,143,037 A | 11/2000 | Goldstein et al. | |
| 6,143,314 A | 11/2000 | Chandrashekar et al. | |
| 6,146,356 A | 11/2000 | Wang et al. | |
| 6,146,404 A | 11/2000 | Kim et al. | |
| 6,153,252 A | 11/2000 | Hossainy et al. | |
| 6,171,327 B1 | 1/2001 | Daniel et al. | |
| 6,190,699 B1 | 2/2001 | Luzzi et al. | |
| 6,206,914 B1 | 3/2001 | Soykan et al. | |
| 6,231,600 B1 | 5/2001 | Zhong et al. | |
| 6,245,104 B1 | 6/2001 | Alt | |
| 6,248,127 B1 | 6/2001 | Shah et al. | |
| 6,248,129 B1 | 6/2001 | Froix | |
| 6,273,913 B1 | 8/2001 | Wright et al. | |
| 6,284,758 B1 | 9/2001 | Egi et al. | |
| 6,309,669 B1 | 10/2001 | Setterstrom et al. | |
| 6,319,541 B1 | 11/2001 | Pletcher et al. | |
| 6,336,934 B1 | 1/2002 | Gilson et al. | |
| 6,342,062 B1 | 1/2002 | Suon et al. | |
| 6,355,691 B1 | 3/2002 | Goodman | |
| 6,358,556 B1 | 3/2002 | Ding et al. | |
| 6,361,819 B1 | 3/2002 | Tedeschi et al. | |
| 6,364,903 B2 | 4/2002 | Tseng et al. | |
| 6,368,658 B1 | 4/2002 | Schwartz et al. | |
| 6,372,246 B1 | 4/2002 | Wei et al. | |
| 6,387,121 B1 | 5/2002 | Alt | |
| 6,409,716 B1 | 6/2002 | Sahatjian et al. | |
| 6,414,050 B1 | 7/2002 | Howdle et al. | |
| 6,416,779 B1 | 7/2002 | D-Augustine et al. | |
| 6,448,315 B1 | 9/2002 | Lidgren et al. | |
| 6,461,644 B1 | 10/2002 | Jackson et al. | |
| 6,495,163 B1 * | 12/2002 | Jordan | 424/474 |
| 6,497,729 B1 | 12/2002 | Moussy et al. | |
| 6,506,213 B1 | 1/2003 | Mandel et al. | |
| 6,517,860 B1 | 2/2003 | Roser et al. | |
| 6,521,258 B1 | 2/2003 | Mandel et al. | |
| 6,524,698 B1 | 2/2003 | Schmoock | |
| 6,537,310 B1 | 3/2003 | Palmaz et al. | |
| 6,541,033 B1 | 4/2003 | Shah | |
| 6,572,813 B1 | 6/2003 | Zhang et al. | |
| 6,610,013 B1 | 8/2003 | Fenster et al. | |
| 6,627,246 B2 | 9/2003 | Mehta et al. | |
| 6,649,627 B1 | 11/2003 | Cecchi et al. | |
| 6,660,176 B2 | 12/2003 | Tepper et al. | |
| 6,669,785 B2 | 12/2003 | DeYoung et al. | |
| 6,669,980 B2 | 12/2003 | Hanson et al. | |
| 6,670,407 B2 | 12/2003 | Howdle et al. | |
| 6,682,757 B1 | 1/2004 | Wright | |
| 6,706,283 B1 | 3/2004 | Appel et al. | |
| 6,710,059 B1 | 3/2004 | Labrie et al. | |
| 6,720,003 B2 | 4/2004 | Cheng et al. | |
| 6,726,712 B1 | 4/2004 | Raeder-Devens et al. | |
| 6,736,996 B1 | 5/2004 | Carbonell et al. | |
| 6,743,505 B2 | 6/2004 | Antall et al. | |
| 6,749,902 B2 | 6/2004 | Yonker et al. | |
| 6,755,871 B2 | 6/2004 | Damaso et al. | |
| 6,756,084 B2 | 6/2004 | Fulton et al. | |
| 6,767,558 B2 | 7/2004 | Wang et al. | |
| 6,780,475 B2 * | 8/2004 | Fulton et al. | 427/458 |
| 6,794,902 B2 | 9/2004 | Becker et al. | |
| 6,800,663 B2 | 10/2004 | Asgarzadeh et al. | |
| 6,815,218 B1 | 11/2004 | Jacobson et al. | |
| 6,837,611 B2 | 1/2005 | Kuo et al. | |
| 6,838,089 B1 | 1/2005 | Carlsson et al. | |
| 6,838,528 B2 | 1/2005 | Zhou et al. | |
| 6,858,598 B1 | 2/2005 | McKearn et al. | |
| 6,860,123 B1 | 3/2005 | Uhlin et al. | |
| 6,884,377 B1 | 4/2005 | Burnham et al. | |
| 6,884,823 B1 | 4/2005 | Plerick et al. | |
| 6,897,205 B2 | 5/2005 | Beckert et al. | |
| 6,905,555 B2 | 6/2005 | DeYoung et al. | |
| 6,908,624 B2 | 6/2005 | Hossainy et al. | |
| 6,916,800 B2 | 7/2005 | McKearn et al. | |
| 6,923,979 B2 | 8/2005 | Fotland et al. | |
| 6,939,569 B1 | 9/2005 | Green et al. | |
| 6,973,718 B2 * | 12/2005 | Sheppard et al. | 29/846 |
| 7,148,201 B2 | 12/2006 | Stern et al. | |
| 7,152,452 B2 | 12/2006 | Kokish | |
| 7,160,592 B2 | 1/2007 | Rypacek et al. | |
| 7,163,715 B1 | 1/2007 | Kramer | |
| 7,169,404 B2 | 1/2007 | Hossainy et al. | |
| 7,171,255 B2 | 1/2007 | Holupka et al. | |
| 7,201,750 B1 | 4/2007 | Eggers et al. | |
| 7,201,940 B1 | 4/2007 | Kramer | |
| 7,229,837 B2 | 6/2007 | Chen | |
| 7,279,174 B2 | 10/2007 | Pacetti et al. | |
| 7,282,020 B2 | 10/2007 | Kaplan | |
| 7,308,748 B2 | 12/2007 | Kokish | |
| 7,326,734 B2 | 2/2008 | Zi et al. | |
| 7,378,105 B2 | 5/2008 | Burke et al. | |
| 7,419,696 B2 | 9/2008 | Berg et al. | |
| 7,429,378 B2 | 9/2008 | Serhan et al. | |
| 7,444,162 B2 | 10/2008 | Hassan | |
| 7,455,688 B2 | 11/2008 | Furst et al. | |
| 7,456,151 B2 | 11/2008 | Li et al. | |
| 7,462,593 B2 | 12/2008 | Cuttitta et al. | |
| 7,485,113 B2 | 2/2009 | Varner et al. | |

(56) References Cited

U.S. PATENT DOCUMENTS

| | | | |
|---|---|---|---|
| 7,524,865 B2 | 4/2009 | D'Amato et al. | |
| 7,537,610 B2 | 5/2009 | Reiss | |
| 7,537,785 B2 | 5/2009 | Loscalzo et al. | |
| 7,553,827 B2 | 6/2009 | Attawia et al. | |
| 7,713,538 B2 | 5/2010 | Lewis et al. | |
| 7,727,275 B2 | 6/2010 | Betts et al. | |
| 7,763,277 B1 | 7/2010 | Canham et al. | |
| 7,837,726 B2 | 11/2010 | Von Oepen et al. | |
| 7,919,108 B2 | 4/2011 | Reyes et al. | |
| 7,955,383 B2 | 6/2011 | Krivoruchko et al. | |
| 7,972,661 B2 | 7/2011 | Pui et al. | |
| 2001/0026804 A1 | 10/2001 | Boutignon | |
| 2001/0034336 A1 | 10/2001 | Shah et al. | |
| 2001/0044629 A1 | 11/2001 | Stinson | |
| 2001/0049551 A1 | 12/2001 | Tseng et al. | |
| 2002/0007209 A1 | 1/2002 | Scheerder et al. | |
| 2002/0051845 A1 | 5/2002 | Mehta et al. | |
| 2002/0082680 A1 | 6/2002 | Shanley et al. | |
| 2002/0091433 A1 | 7/2002 | Ding et al. | |
| 2002/0099332 A1 | 7/2002 | Slepian et al. | |
| 2002/0125860 A1 | 9/2002 | Schworm et al. | |
| 2002/0133072 A1 | 9/2002 | Wang et al. | |
| 2002/0144757 A1 | 10/2002 | Craig et al. | |
| 2003/0001830 A1 | 1/2003 | Wampler et al. | |
| 2003/0031699 A1 | 2/2003 | Van Antwerp | |
| 2003/0077200 A1 | 4/2003 | Craig et al. | |
| 2003/0088307 A1 | 5/2003 | Shulze et al. | |
| 2003/0125800 A1 | 7/2003 | Shulze et al. | |
| 2003/0143315 A1 | 7/2003 | Pui et al. | |
| 2003/0170305 A1 | 9/2003 | O'Neil et al. | |
| 2003/0180376 A1 | 9/2003 | Dalal et al. | |
| 2003/0185964 A1* | 10/2003 | Weber et al. | 427/2.25 |
| 2003/0204238 A1 | 10/2003 | Tedeschi | |
| 2003/0222017 A1 | 12/2003 | Fulton et al. | |
| 2003/0222018 A1 | 12/2003 | Yonker et al. | |
| 2003/0232014 A1 | 12/2003 | Burke et al. | |
| 2004/0013792 A1 | 1/2004 | Epstein et al. | |
| 2004/0018228 A1 | 1/2004 | Fischell et al. | |
| 2004/0022853 A1 | 2/2004 | Ashton et al. | |
| 2004/0044397 A1 | 3/2004 | Stinson | |
| 2004/0059290 A1 | 3/2004 | Palasis et al. | |
| 2004/0106982 A1 | 6/2004 | Jalisi | |
| 2004/0122205 A1 | 6/2004 | Nathan | |
| 2004/0126542 A1 | 7/2004 | Fujiwara et al. | |
| 2004/0143317 A1 | 7/2004 | Stinson et al. | |
| 2004/0157789 A1 | 8/2004 | Geall | |
| 2004/0170685 A1 | 9/2004 | Carpenter et al. | |
| 2004/0193177 A1 | 9/2004 | Houghton et al. | |
| 2004/0193262 A1 | 9/2004 | Shadduck | |
| 2004/0220660 A1 | 11/2004 | Shanley et al. | |
| 2004/0224001 A1 | 11/2004 | Pacetti et al. | |
| 2004/0236416 A1 | 11/2004 | Falotico | |
| 2004/0260000 A1* | 12/2004 | Chaiko | 524/445 |
| 2005/0003074 A1 | 1/2005 | Brown et al. | |
| 2005/0004661 A1 | 1/2005 | Lewis et al. | |
| 2005/0010275 A1 | 1/2005 | Sahatjian et al. | |
| 2005/0015046 A1 | 1/2005 | Weber et al. | |
| 2005/0019747 A1 | 1/2005 | Anderson et al. | |
| 2005/0038498 A1 | 2/2005 | Dubrow et al. | |
| 2005/0048121 A1 | 3/2005 | East et al. | |
| 2005/0049694 A1 | 3/2005 | Neary | |
| 2005/0069630 A1 | 3/2005 | Fox et al. | |
| 2005/0070990 A1 | 3/2005 | Stinson | |
| 2005/0075714 A1 | 4/2005 | Cheng et al. | |
| 2005/0079199 A1 | 4/2005 | Heruth et al. | |
| 2005/0079274 A1 | 4/2005 | Palasis et al. | |
| 2005/0084533 A1 | 4/2005 | Howdle et al. | |
| 2005/0131513 A1 | 6/2005 | Myers et al. | |
| 2005/0147734 A1 | 7/2005 | Seppala et al. | |
| 2005/0166841 A1 | 8/2005 | Robida | |
| 2005/0175772 A1 | 8/2005 | Worsham et al. | |
| 2005/0177223 A1 | 8/2005 | Palmaz | |
| 2005/0191491 A1 | 9/2005 | Wang et al. | |
| 2005/0196424 A1 | 9/2005 | Chappa | |
| 2005/0208102 A1 | 9/2005 | Schultz | |
| 2005/0216075 A1 | 9/2005 | Wang et al. | |
| 2005/0238829 A1 | 10/2005 | Motherwell et al. | |
| 2005/0255327 A1 | 11/2005 | Chaney | |
| 2005/0260186 A1 | 11/2005 | Bookbinder et al. | |
| 2005/0268573 A1* | 12/2005 | Yan | 53/425 |
| 2005/0288481 A1 | 12/2005 | Desnoyer et al. | |
| 2006/0001011 A1 | 1/2006 | Wilson et al. | |
| 2006/0020325 A1 | 1/2006 | Burgermeister et al. | |
| 2006/0030652 A1* | 2/2006 | Adams et al. | 524/210 |
| 2006/0045901 A1 | 3/2006 | Weber et al. | |
| 2006/0089705 A1 | 4/2006 | Ding et al. | |
| 2006/0093771 A1 | 5/2006 | Rypacek et al. | |
| 2006/0094744 A1 | 5/2006 | Maryanoff et al. | |
| 2006/0116755 A1 | 6/2006 | Stinson | |
| 2006/0121089 A1 | 6/2006 | Michal et al. | |
| 2006/0134211 A1 | 6/2006 | Lien et al. | |
| 2006/0136041 A1 | 6/2006 | Schmid et al. | |
| 2006/0147698 A1* | 7/2006 | Carroll et al. | 428/316.6 |
| 2006/0153729 A1 | 7/2006 | Stinson | |
| 2006/0160455 A1 | 7/2006 | Sugyo et al. | |
| 2006/0188547 A1 | 8/2006 | Bezwada | |
| 2006/0193886 A1 | 8/2006 | Owens et al. | |
| 2006/0193890 A1 | 8/2006 | Owens et al. | |
| 2006/0198868 A1 | 9/2006 | DeWitt et al. | |
| 2006/0210638 A1 | 9/2006 | Liversidge et al. | |
| 2006/0216324 A1 | 9/2006 | Stucke et al. | |
| 2006/0222756 A1 | 10/2006 | Davila et al. | |
| 2006/0228415 A1* | 10/2006 | Oberegger et al. | 424/472 |
| 2006/0276877 A1 | 12/2006 | Owens et al. | |
| 2007/0009564 A1 | 1/2007 | McClain et al. | |
| 2007/0032864 A1 | 2/2007 | Furst et al. | |
| 2007/0038227 A1 | 2/2007 | Massicotte et al. | |
| 2007/0059350 A1 | 3/2007 | Kennedy et al. | |
| 2007/0110888 A1 | 5/2007 | Radhakrishnan et al. | |
| 2007/0123973 A1 | 5/2007 | Roth et al. | |
| 2007/0123977 A1 | 5/2007 | Cottone et al. | |
| 2007/0128274 A1* | 6/2007 | Zhu et al. | 424/464 |
| 2007/0148251 A1 | 6/2007 | Hossainy et al. | |
| 2007/0196423 A1 | 8/2007 | Ruane et al. | |
| 2007/0198081 A1 | 8/2007 | Castro et al. | |
| 2007/0203569 A1 | 8/2007 | Burgermeister et al. | |
| 2007/0259017 A1 | 11/2007 | Francis | |
| 2007/0280992 A1 | 12/2007 | Margaron et al. | |
| 2008/0051866 A1 | 2/2008 | Chen et al. | |
| 2008/0071359 A1 | 3/2008 | Thornton et al. | |
| 2008/0075753 A1 | 3/2008 | Chappa | |
| 2008/0077232 A1 | 3/2008 | Nishide | |
| 2008/0095919 A1 | 4/2008 | McClain et al. | |
| 2008/0097575 A1 | 4/2008 | Cottone | |
| 2008/0097591 A1* | 4/2008 | Savage et al. | 623/1.43 |
| 2008/0107702 A1 | 5/2008 | Jennissen | |
| 2008/0118543 A1 | 5/2008 | Pacetti et al. | |
| 2008/0124372 A1 | 5/2008 | Hossainy et al. | |
| 2008/0138375 A1 | 6/2008 | Yan et al. | |
| 2008/0206304 A1 | 8/2008 | Lindquist et al. | |
| 2008/0213464 A1 | 9/2008 | O'Connor | |
| 2008/0255510 A1 | 10/2008 | Wang | |
| 2008/0269449 A1 | 10/2008 | Chattopadhyay et al. | |
| 2008/0292776 A1 | 11/2008 | Dias et al. | |
| 2008/0300669 A1 | 12/2008 | Hossainy | |
| 2009/0043379 A1 | 2/2009 | Prescott | |
| 2009/0062909 A1 | 3/2009 | Taylor et al. | |
| 2009/0068266 A1 | 3/2009 | Raheja et al. | |
| 2009/0076446 A1 | 3/2009 | Dubuclet et al. | |
| 2009/0082855 A1 | 3/2009 | Borges et al. | |
| 2009/0098178 A1 | 4/2009 | Hofmann et al. | |
| 2009/0105809 A1 | 4/2009 | Lee et al. | |
| 2009/0110711 A1 | 4/2009 | Trollsas et al. | |
| 2009/0111787 A1 | 4/2009 | Lim et al. | |
| 2009/0123515 A1* | 5/2009 | Taylor et al. | 424/423 |
| 2009/0186069 A1 | 7/2009 | DeYoung et al. | |
| 2009/0202609 A1 | 8/2009 | Keough et al. | |
| 2009/0216317 A1 | 8/2009 | Cromack et al. | |
| 2009/0227949 A1 | 9/2009 | Freyman et al. | |
| 2009/0231578 A1 | 9/2009 | Ling et al. | |
| 2009/0263460 A1 | 10/2009 | McDonald | |
| 2009/0285974 A1 | 11/2009 | Kerrigan | |
| 2009/0292351 A1 | 11/2009 | McClain et al. | |
| 2009/0297578 A1 | 12/2009 | Trollsas et al. | |

(56) References Cited

U.S. PATENT DOCUMENTS

| | | |
|---|---|---|
| 2010/0015200 A1 | 1/2010 | McClain et al. |
| 2010/0030261 A1 | 2/2010 | McClain |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0272778 A1 | 10/2010 | McClain et al. |
| 2010/0298928 A1 | 11/2010 | McClain et al. |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja |
| 2011/0190864 A1 | 8/2011 | McClain et al. |
| 2011/0238161 A1 | 9/2011 | Fulton et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0172787 A1 | 7/2012 | McClain et al. |
| 2012/0177742 A1 | 7/2012 | McClain et al. |
| 2012/0271396 A1 | 10/2012 | Zheng et al. |
| 2012/0280432 A1 | 11/2012 | Chen et al. |
| 2012/0323311 A1 | 12/2012 | McClain et al. |

FOREIGN PATENT DOCUMENTS

| | | |
|---|---|---|
| CN | 1649551 | 8/2005 |
| EP | 0604022 | 6/1994 |
| EP | 0982041 | 3/2000 |
| EP | 1195822 A2 | 4/2002 |
| EP | 1454677 | 9/2004 |
| EP | 2197070 A1 | 6/2010 |
| EP | 2293357 A1 | 3/2011 |
| EP | 2293366 A1 | 3/2011 |
| JP | 1994-098902 | 4/1994 |
| JP | H09-056807 | 3/1997 |
| JP | 2003533492 | 11/2001 |
| JP | 2003-205037 | 7/2003 |
| JP | 2003-533286 | 11/2003 |
| JP | 2003-533493 | 11/2003 |
| JP | 2004/173770 | 6/2004 |
| JP | 2004-518458 | 6/2004 |
| JP | 2004-529674 | 9/2004 |
| JP | 2005-505318 | 2/2005 |
| JP | 2005-523119 | 8/2005 |
| JP | 2005-523332 | 8/2005 |
| JP | 2005-296690 | 10/2005 |
| JP | 2009-501566 | 1/2009 |
| KR | 10-2004-0034064 | 4/2004 |
| WO | WO-95/06487 | 3/1995 |
| WO | WO 96/20698 | 7/1996 |
| WO | WO 97/45502 | 12/1997 |
| WO | WO-01/54662 | 8/2001 |
| WO | WO-01-87371 | 11/2001 |
| WO | WO-01/87372 | 11/2001 |
| WO | WO-02/40702 | 5/2002 |
| WO | WO-02/43799 | 6/2002 |
| WO | WO-02/090085 | 11/2002 |
| WO | WO-03/039553 | 5/2003 |
| WO | WO-03/101624 A1 | 12/2003 |
| WO | WO-2004/028589 | 4/2004 |
| WO | WO-2004/043506 | 5/2004 |
| WO | WO-2004/045450 | 6/2004 |
| WO | WO-2004/098574 | 11/2004 |
| WO | WO-2005-42623 A1 | 5/2005 |
| WO | WO-2005/063319 | 7/2005 |
| WO | WO-2005/069889 | 8/2005 |
| WO | WO-2005-117942 A2 | 12/2005 |
| WO | WO-2006/014534 | 2/2006 |
| WO | WO-2006/052575 | 5/2006 |
| WO | WO-2006/065685 | 6/2006 |
| WO | WO-2006-083796 A2 | 8/2006 |
| WO | WO-2006-099276 A2 | 9/2006 |
| WO | WO-2007-002238 | 1/2007 |
| WO | WO-2007-011707 A2 | 1/2007 |
| WO | WO-2007-011707 A3 | 1/2007 |
| WO | WO-2007-011708 A2 | 1/2007 |
| WO | WO-2007-011708 A3 | 1/2007 |
| WO | WO-2007-127363 A2 | 1/2007 |
| WO | WO-2007/092179 | 8/2007 |
| WO | WO 2007/143609 | 12/2007 |
| WO | WO-2008/042909 | 4/2008 |
| WO | WO-2008-046641 | 4/2008 |
| WO | WO-2008-046642 | 4/2008 |
| WO | WO-2008/052000 | 5/2008 |
| WO | WO-2008/070996 | 6/2008 |
| WO | WO 2008/086369 | 7/2008 |
| WO | WO-2008-131131 A1 | 10/2008 |
| WO | WO-2008/148013 | 12/2008 |
| WO | WO 2009/051780 | 4/2009 |
| WO | WO-2009/146209 | 12/2009 |
| WO | WO 2010/009335 | 1/2010 |
| WO | WO-2010/075590 | 7/2010 |
| WO | WO-2010-111196 A2 | 9/2010 |
| WO | WO-2010-111196 A3 | 9/2010 |
| WO | WO-2010-111232 A3 | 9/2010 |
| WO | WO-2010-111232 A9 | 9/2010 |
| WO | WO-2010-111238 A2 | 9/2010 |
| WO | WO-2010-111238 A3 | 9/2010 |
| WO | WO-2010-120552 A2 | 10/2010 |
| WO | WO 2010-120552 A3 | 10/2010 |
| WO | WO-2010-121187 A2 | 10/2010 |
| WO | WO-2010-121187 A3 | 10/2010 |
| WO | WO-2011-009096 A1 | 1/2011 |
| WO | WO-2011/097103 | 8/2011 |
| WO | WO-2011/119762 | 9/2011 |
| WO | WO-2011/130448 | 10/2011 |
| WO | WO-2011/133655 | 10/2011 |
| WO | WO-2012/009684 | 1/2012 |
| WO | WO-2012/034079 | 3/2012 |
| WO | WO-2012/082502 | 6/2012 |
| WO | WO-2012/092504 | 7/2012 |
| WO | WO-2012/142319 | 10/2012 |
| WO | WO-2012/166819 | 12/2012 |
| WO | WO-2013/012689 | 1/2013 |
| WO | WO-2013/025535 | 2/2013 |
| WO | WO-2013/059509 | 4/2013 |
| WO | WO-2013/173657 | 11/2013 |
| WO | WO-2013/177211 | 11/2013 |
| WO | WO-2014/063111 | 4/2014 |

OTHER PUBLICATIONS

Khayankarn et al. Adhesion and permeability of polyimide—clay nanocomposite films for protective coatings Journal of Polymer Science. 2003. vol. 89 Issue 11 pp. 2875-2881.*

PCT/US2011/032371, International Search Report dated Jul. 7, 2011.

Domingo, C. et al., "Precipication of ultrafine organic crystals from the rapid expansion of supercritical solutions over a capillary and a frit nozzle," J. Supercritical Fluids 10:39-55 (1997).

McAlpine, J.B. et al., "Revised NMR Assignments for Rapamycin," J. Antibiotics 44:688-690 (1991).

(56) References Cited

OTHER PUBLICATIONS

Ong and Serruys, "Technology Insight: an overview of research in drug-eluting stents," Nat. Clin. Parct. Cardiovas. Med. 2(12):647-658 (2005).
Schrieber, S.L. et al., J. Am. Chem. Soc. 113:7433 (1991).
PCT/US07/82275 Search Report mailed Apr. 18, 2008.
PCT/US06/27322 Search Report mailed Apr. 25, 2007.
PCT/US06/27321 Search Report mailed Oct. 16, 2007.
PCT/US06/24221 Search Report mailed Jan. 29, 2007.
PCT/US07/10227 Search Report mailed Aug. 8, 2008.
PCT/US09/41045 Search Report dated Aug. 11, 2009.
PCT/US08/11852 Search Report dated Dec. 19, 2008.
PCT/US08/64732 Search Report dated Sep. 4, 2008.
PCT/US08/60671 Search Report dated Sep. 5, 2008.
PCT/US08/50536 Search Report dated Jun. 2, 2008.
PCT/US07/80213 Search Report dated Apr. 16, 1008.
PCT/US09/50883 Search Report dated Nov. 17, 2009.
Schmidt et al., "A Comparison of the Mechanical Performance Characteristics of Seven Drug-Eluting Stent Systems," Catheterization and Cardiovascular Interventions 73:350-360 (2009).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Szabadits et al., "Flexibility and trackability of laser cut coronary stent systems," Acta of Bioengineering and Biomechanics 11(3):11-18 (2009).
PCT/US10/42355 Search Report mailed Sep. 2, 2010.
PCT/US10/28253 Search Report and Written Opinion mailed Dec. 6, 2010.
PCT/US10/28265 Search Report and Written Opinion mailed Dec. 13, 2010.
U.S. Appl. No. 11/158,724 Office Action Mailed Sep. 8, 2008.
AU2006270221 Exam Report dated Apr. 6, 2010.
AU2011232760 Exam Report dated Apr. 10, 2013.
AU2012203203 Exam Report dated Apr. 12, 2013.
AU2007243268 Exam Report dated May 15, 2013.
CA 2759015 Office action dated Apr. 8, 2013.
CA 2756388 Office Action dated Apr. 11, 2013.
Chlopek et al. "The influence of carbon fibres on the resorption time and mechanical properties of the lactide—glycolide co-polymer." J. Biomater. Sci. Polymer Edn, vol. 18, No. 11, pp. 1355-1368 (2007).
CN 200880100102.3 Office Action dated Apr. 11, 2013.
Cohen, et al. "Sintering Technique for the Preparation of Polymer Matrices fro the Controlled Release of Macromolecules." Journal of Pharamceutical Sciences, vol. 73, No. 8, 1984, p. 1034-1037.
EP07756094.4 Office action dated May 29, 2013.
IN-368/DELNP/2008 Exam Report dated Oct. 17, 2011.
IL-208648 Official Notification dated Feb. 9, 2012.
JP-2009-534823 Office Action dated Apr. 23, 2013.
Koh et al. "A novel nanostructured poly(lactic-co-glycolic-acid)—multi-walled carbon nanotube composite for blood-contacting applications: Thrombogenicity studies.".
NZ 588549 Examination Report dated Mar. 28, 2011.
Sahajanand Medical Technologies (Supralimus Core; Jul. 6, 2008).
U.S. Appl. No. 13/605,904 Office Action Mailed Nov. 27, 2012.
U.S. Appl. No. 13/384,216 Office action Mailed Apr. 24, 2013.
U.S. Appl. No. 13/340,472 Office action Mailed Apr. 26, 2013.
U.S. Appl. No. 12/729,156 Office action Mailed May 8, 2013.
U.S. Appl. No. 13/014,632 Office action Mailed May 8, 2013.
U.S. Appl. No. 13/086,335 Office action Mailed May 22, 2013.
U.S. Appl. No. 11/158,724 Office action Mailed May 23, 2013.
U.S. Appl. No. 12/298,459 Office Action Mailed May 31, 2013.
Wu et al., "Study on the preparation and characterization of biodegradable polylactide/multi-walled carbon nanotubes nanocomposites." Polymer 48 (2007) 4449-4458.
PCT/US10/31470 Search Report and Written Opinion mailed Jan. 28, 2011.
AU2012203577 Exam Report dated Jun. 7, 2013.
AU2011256902 Exam Report dated Jun. 13, 2013.
CA 2730995 Office action dated May 29, 2013.
CA 2650590 Office action dated Jul. 23, 2013.
CN 200880007308.1 Office Action dated Jul. 3, 2013.
CN 200880020515 Office Action dated Jul. 22, 2013.
EP08733210.2 Office action dated Jul. 16, 2013.
EP11769546.0 Search Report dated Sep. 19, 2013.
EP09798764.8 Search Report dated Sep. 30, 2013.
JP-2011-505248 Office action dated Jun. 4, 2013.
JP-2010-510441 Office action dated May 7, 2013.
JP-2009-545647 Office Action dated May 14, 2013.
KR10-2008-7003756 Office Action dated Sep. 23, 2013.
Shekunov et al. "Crystallization Processes in Pharmaceutical Technology and Drug Delivery Design." Journal of Crystal Growth 211 (2000), pp. 122-136.
U.S. Appl. No. 13/229,473 Office Action Mailed Jun. 17, 2013.
U.S. Appl. No. 13/605,904 Office Action Mailed Jun. 28, 2013.
U.S. Appl. No. 11/877,591 Office Action Mailed Jul. 1, 2013.
U.S. Appl. No. 12/748,134 Office Action Mailed Jul. 18, 2013.
U.S. Appl. No. 12/738,411 Office action Mailed Aug. 21, 2013.
U.S. Appl. No. 12/522,379 Final Office Action Mailed Aug. 28, 2013.
U.S. Appl. No. 12/648,106 Office Action Mailed Sep. 18, 2013.
PCT/US2011/29667 International Search Report and Written Opinion mailed Jun. 1, 2011.
PCT/US2011/67921 International Preliminary Report on Patentability dated Jul. 11, 2013.
Abreu Filho et al., "Influence of metal alloy and the profile of coronary stents in patients with multivessel coronary disease," Clinics 2011;66(6):985-989.
CA 2615452 Office Action dated Oct. 8, 2013.
CA 2756386 Office action dated Oct. 24, 2013.
CA 2613280 Office action dated Dec. 10, 2013.
CN 200880100102.3 Office Action dated Dec. 11, 2013.
CN 200980136432.2 Office action dated Nov. 4, 2013.
Colombo et al. "Selection of Coronary Stents," Journal of the American College of Cardiology, vol. 40, No. 6, 2002, p. 1021-1033.
EA 200901254 Office Action dated Jul. 29, 2013.
EA 201001497 Office Action dated Jul. 29, 2013.
EP08705772.5 Office Action dated Oct. 30, 2013.
EP09755571.8 Office Action dated Dec. 13, 2013.
EP10756696.0 Search Report dated Oct. 10, 2013.
EP10764884.2 Search Report dated Oct. 28, 2013.
EP10765295.0 Search Report dated Oct. 17, 2013.
IN-6884DEFNP2009 Office Action dated Oct. 31, 2013.
IL-201550 Official Notification dated Dec. 8, 2013.
JP-2012-503677 Office action dated Nov. 1, 2013.
JP-2012-151964 Office Action dated Dec. 10, 2013.
PCT/US06/24221 International Preliminary Report on Patentability dated Dec. 24, 2007.
PCT/US06/27321 International Preliminary Report on Patentability dated Jan. 16, 2008.
PCT/US06/27322 International Preliminary Report on Patentability dated Jan. 16, 2008.
PCT/US07/10227 International Preliminary Report on Patentability dated Oct. 28, 2008.
PCT/US07/80213 International Preliminary Report on Patentability dated Apr. 7, 2009.
PCT/US08/11852 International Preliminary Report on Patentability dated Apr. 20, 2010.
PCT/US08/50536 International Preliminary Report on Patentability dated Jul. 14, 2009.
PCT/US08/60671 International Preliminary Report on Patentability dated Oct. 20, 2009.
PCT/US08/64732 International Preliminary Report on Patentability dated Dec. 1, 2009.
PCT/US09/41045 International Preliminary Report on Patentability dated Oct. 19, 2010.
PCT/US09/69603 International Preliminary Report on Patentability dated Jun. 29, 2011.
PCT/US10/28265 International Report on Patentability dated Sep. 27, 2011.
PCT/US10/29494 International Preliminary Report on Patentability dated Oct. 4, 2011.

(56) References Cited

OTHER PUBLICATIONS

PCT/US10/31470 International Preliminary Report on Patentability dated Oct. 18, 2011.
PCT/US11/032371 International Report on Patentability dated Oct. 16, 2012.
PCT/US11/051092 International Search Report dated Apr. 2, 2012.
PCT/US11/051092 Written Opinion dated Mar. 9, 2013.
PCT/US11/22623 International Preliminary Report on Patentability dated Aug. 7, 2012.
PCT/US11/29667 International Search Report and Written Opinion mailed Jun. 1, 2011.
PCT/US11/67921 International Preliminary Report on Patentability dated Jul. 11, 2013.
PCT/US12/33367 International Preliminary Report on Patentability dated Oct. 15, 2013.
U.S. Appl. No. 11/158,724 Office action Mailed Dec. 31, 2013.
U.S. Appl. No. 11/877,591 Final Action dated Nov. 4, 2013.
U.S. Appl. No. 12/595,848 Office Action Mailed Oct. 22, 2013.
U.S. Appl. No. 12/729,580 Final Action dated Nov. 14, 2013.
U.S. Appl. No. 12/751,902 Office Action Mailed Dec. 19, 2013.
U.S. Appl. No. 12/762,007 Final Office action Mailed Oct. 22, 2013.
U.S. Appl. No. 13/340,472 Office action Mailed Jan. 15, 2014.
U.S. Appl. No. 13/384,216 Final Action dated Nov. 6, 2013.
U.S. Appl. No. 13/014,632 Office action Mailed Jan. 10, 2014.
Zilberman et al., Drug-Eluting bioresorbable stents for various applications, Annu Rev Biomed Eng., 2006;8:158-180.
Akoh et al, "One-Stage Synthesis of Raffinose Fatty Acid Polyesters. "Journal Food Science (1987) 52:1570.
Albert et al., "Antibiotics for preventing recurrent urinary tract infection in non-pregnant women,"Cochrane Database System Rev. 3, CD001209 (2004).
Au et al., "Methods to improve efficacy of intravesical mitomycin C: Results of a randomized phase III trial," Journal of the National Cancer Institute, 93(8), 597-604 (2001).
AU2007243268 Exam Report dated Aug. 31, 2011.
AU2009251504 Exam Report dated Dec. 8, 2011.
AU2009270849 Exam Report dated Feb. 14, 2012.
Balss et al., "Quantitative spatial distribution of sirolumus and polymers in drug-eluting stents using confocal Raman microscopy," J. of Biomedical Materials Research Part A, 258-270 (2007).
Belu et al., "Three-Dimensional Compositional Analysis of Drug Eluting Stent Coatings Using Cluster Secondary Ioan Mass Spectroscopy," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatement of urinary tract infection with probiotics: Review and research perspective," Indian Journal Urol. 24(2):139-144 (2008).
Brunstein et al., "Histamine, a vasoactive agent with vascular disrupting potential improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. (2007) Wiley and Sons.
CA 2615452 Office Action dated Dec. 19, 2012.
CA 2684482 Office Action Jul. 11, 2012.
CA 2684482 Office Action dated Nov. 10, 2011.
CA 2688314 Office Action dated Jun. 6, 2012.
CA 2730995 Office Action dated Sep. 26, 2012.
CA 2757276 Office Action dated Feb. 15, 2013.
CA 2756307 Office action dated Feb. 18, 2013.
CA 2756386 Office action dated Mar. 15, 2013.
CA 2613280 Office Action dated Oct. 2, 2012.
Cadieux et al., "Use of triclosan-eluting ureteral stents in patients with long-term stents," J. Endourol (Epub) (Jun. 19, 2009).
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al. Immobilization of heparin on a silicone surface through a heterobifunctional PEG spacer. Biomaterials. Dec. 2005;26(35):7418-24.
Clair and Burks, "Thermoplastic/Melt-Processable Polyimides," NASA Conf. Pub. #2334 (1984), pp. 337-355.
CN 2006800258093 Office Action dated May 30, 2012.
CN 200880007308.1 Office Action dated Nov. 23, 2011.
CN 200880007308.1 Office Action dated Oct. 18, 2012.
CN 200880020515 Office Action dated Oct. 9, 2012.
CN 200880100102.3 Office Action dated Jun. 1, 2012.
CN 200980122691 Office Action dated Oct. 10, 2012.
CN 200780047425.6 Office action dated Aug. 3, 2012.
CN 200780047425.6 Office action dated Feb. 28, 2013.
CN 200980136432.2 Office action dated Jan. 14, 2013.
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury," Arterioscler Thromb Vasc Biol 2008;28:820-826.
Derwent-Acc-No. 2004-108578 Abstracting 2004003077; Jan. 8, 2004; 3 pages.
DiStasi et al., "Percutaneous sequential Bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides. "J. Polym Sci. 25:3373-3386 (1987).
Dzik-Jurasz, "Molecular imaging in vivo: an introduction," The British Journal of Radiology, 76:S98-S109 (2003).
EA 201001497 Office Action dated Feb. 11, 2013.
EA 200901254/28 Office Action dated Jul. 18, 2012.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Search Report dated Feb. 6, 2012.
EP07756094.4 Search Report dated Aug. 31, 2012.
EP08733210.2 Search Report dated Oct. 23, 2012.
EP08756215.3 Search Report dated Oct. 5, 2011.
EP08756215.3 Search Report dated Jan. 28, 2013.
EP09805981.9 Office Action dated Feb. 13, 2013.
EP06787258.0 Office Action dated Mar. 15, 2013.
EP09755571.8 Search Report dated Apr. 9, 2013.
EP08705772.5 Search Report dated Feb. 20, 2013.
Ettmayer et al. Lessons learned from marketed and investigational prodrugs. J Med Chem. May 6, 2004;47(10):2393-404.
Fibbi et al., "Chronic inflammation in the pathogenesis of benign prostatic hyperplasia," Int J Androl. Jun. 1, 2010;33(3):475-88.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," Oct. 29, 2008, NeuroReport 19(16):1585-1588.
Fulton et al. Thin Fluoropolymer films and nanoparticle coatings from the rapid expansion of supercritical carbon dioxide solutions with electrostatic collection, Polymer Communication. 2003; 2627-3632.
Griebenow et al., "On Protein Denaturation in Aqueous-Organic Mixtures but not in Pure Organic Solvents," J. Am Chem Soc., vol. 118. No. 47, 11695-11700 (1996).

(56) References Cited

OTHER PUBLICATIONS

Hamilos et al., "Differential effects of Drug-Eluting Stents on Local Endothelium-Dependent Coronary Vasomotion." JACC vol. 51, No. 22, 2008, Endothelium and DES Jun. 3, 2008:2123-9.
Hartmann et al., "Tubo-ovarian abscess in virginal adolescents: exposure oldie underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 (2003) 2933-2937.
Hinds, WC. Aerosol Technology, Properties, Behavior and Measurement of Airborne Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Iconomidou et al., "Secondary Structure of Chorion Proteins of the Teleosatan Fish *Dentex dentex* by ATR FR-IR and FT-Raman Spectroscopy," J. of Structural Biology, 132, 112-122 (2000).
Jackson et al., "Characterization of perivascular poly(lactic-co-glycolic acid) films containing paclitaxel" *Int. J of Pharmaceutics*, 283:97-109 (2004), incorporated in its entirety herein by reference.
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et al., "Release of Plasmid DNA from Intravascular Stents Coated with Ultrathin Multilayered Polyelectrolyte Films" *Biomacromolecules*. 7: 2483-2491 (2006).
Johns, H.E, J.R.Cunningham, Thomas, Charles C., Publisher, "The Physics of Radiology,"1983, Springfield, IL, pp. 133-143.
Joner et al. "Site-specific targeting of nanoparticle prednisolone reduces in-stent restenosis in a rabbit model of established atheroma," Arterioscler Thromb Vasc Biol. 2008;28:1960-1966.
Mei et al., "Local Delivery of Modified Paclitaxel-Loaded Poly(ε-caprolactone)/Pluronic F68 Nanoparticles for Long-Term Inhibition of Hyperplasia," Journal of Pharmaceutical Sciences, vol. 98, No. 6, Jun. 2009.
Jovanovic et al. "Stabilization of Proteins in Dry Powder Formulations Using Supercritical Fluid Technology," Pharm. Res. 2004; 21(11).
JP 2008-521633 Office Action dated Oct. 12, 2012.
JP2008-521633 Office Action dated Dec. 28, 2011.
JP-2009-534823 Office Action dated Sep. 20, 2012.
JP-2009-534823 Office Action dated Feb. 2, 2012.
JP-2009-545647 Office Action dated Jun. 5, 2012.
JP-2010-504253 Office Action dated Dec. 12, 2011.
JP-2010-504253 Office Action dated Dec. 7, 2012.
JP-2011-518920 Office action dated Dec. 17, 2012.
JP-2012-503677 Office action dated Jan. 18, 2013.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Khan et al., "Cyclic Acetals of 4,1',6'-Trichloro-4,1',6',-Trideoxy-Trideoxy-galacto-Sucrose and their Conversion into Methyl Ether Derivatives." . Carb. Res. (1990) 198:275-283.
Khan et al., "Chemistry and the new uses of Sucrose: How Important?" Pur and Appl. Chem (1984) 56:833-844.
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters (1933) 34:7767.
Khayankarn et al., "Adhesion and Permeability of Polyimide-Clay Nanocomposite Films for Protective Coatings," Journal of Applied Polymer Science, vol. 89, 2875-2881 (2003).
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.
Lamm et al., "Bladder Cancer: Current Optimal Intravesical Treatment: Pharmacologic Treatment," Urologic Nursing 25(5):323-6, 331-2 (Oct. 26, 2005).
Latella et al., "Nanoindentation hardness. Young's modulus, and creep behavior of organic-inorganic silica-based sol-gel thin films on copper," J Mater Res 23(9): 2357-2365 (2008).
Lehmann et al, "Drug treatment of nonviral sexually transmitted diseases: specific issues in adolescents," Pediatr Drugs 3(7):481-494 (2001.
Mahoney et al., "Three-Dimensional Compositional Analysis of Drug Eluting Stent Coatings Using Cluster Secondary Ion mass Spectrometry," Anal. Chem. , 80, 624-632 (2008).
Mario, C.D. et al., "Drug-Eluting Bioabsorbable Magnesium Stent," J. Interventional Cardiology 16(6):391-395 (2004).
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Melonakos et al., Treatment of low-grade bulbar transitional cell carcinoma with urethral instillation of mitomycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Middleton and Tipton, Synthetic biodegradable polymers as orthopedic devises. Biomaterials 2000; 21 :2335-46.
Minchin, "Nanomedicine: sizing up targets with nanoparticles," Nature Nanotechnology, vol. 33, Jan. 2008, 12-13.
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 2000;46(4):857-65.
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
PCT/US06/27321 International Search Report mailed Oct. 16, 2007.
PCT/US08/60671 International Search Report mailed Sep. 5, 2008.
PCT/US08/64732 international Search Report mailed Sep. 4, 2008.
PCT/US09/41045 International Search Report mailed Aug. 11, 2009.
PCT/US09/50883 International Search Report mailed Nov. 17, 2009.
PCT/US12/46545 international Search Report mailed Nov. 20, 2012.
PCT/US12/50408 International Search Report mailed Oct. 19, 2012.
PCT/US2012/040040 International Search Report mailed Sep. 7, 2012.
Perry et al., Chemical Engineer's Handbook, 5th Edition, McGraw-Hill, New York, 1973; 20-106.
Torchlin, "Micellar Nanocarriers: Pharmaecutial Perspectives," Pharmaceutical Research, vol. 24, No. 1, Jan. 2007.
Plas et al., "Tubers and tumors: rapamycin therapy for benign and malignant tumors", Curr Opin Cell Bio 21: 230-236, (2009).

(56) References Cited

OTHER PUBLICATIONS

Poling et al., The Properties of Gases and Liquids. McGraw-Hill. 2001; 9:1-9.97.
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl):29-33 (2002).
Raganath et al., "Hydrogel matrix entrapping PLGA-paclitaxel microspheres: drug delivery with near zero-order release and implantability advantages for malignant brain tumour," Pharm Res (Epub) Jun. 20, 2009).
Ranade et al., "Physical characterization of controlled release of paclitaxel from the TAXUS Express2 drug-eluting stent," J. Biomed Mater. Res. 71(4):625-634 (2004).
Reddy et al, "Inhibition of apoptosis through localized delivery of rapamycin-loaded nanoparticles prevented neointimal hyperplasia and reendothelialized injured artery," Circ Cardiovasc Interv 2008;1;209-216.
Ristikankare et al., "Sedation, topical pharnygeal anesthesia and cardiorespiratory safety during gastroscopy," J. Clin Gastorenterol. 40(1):899-905 (2006).
Schmidt et al., "In vitro measurement of quality parameters of stent-catheter systems," Biomed Techn 50(S1):1505-1506 (2005).
Schmidt et al., "Trackability, Crossability, and Pushability of Coronary Stent Systems—An Experimental Approach," Biomed Techn 47 (2002), Erg. 1, S. 124-126.
Schreiber, S.L. et al., "Atomic Structure of the Rapamycin Human Immunophilin FKBP-12 Complex," J. Am. Chem. Soc. 113:7433-7435 (1991).
Sen et al., "Topical heparin: A promising agent for the prevention of tracheal stenosis in airway surgery," J. Surg. Res (Epub ahead of print) Feb. 21, 2009.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
SG201007602-4 Written Opinion dated May 25, 2012.
Simpson et al., "Hyaluronan and hyaluronidase in genitourinary tumors."Front Biosci. 13:5664-5680.
Smith et al., "Mitomycin C and the endoscopic treatment of laryngotracheal stenosis: are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008.
Testa, B. Prodrug research: futile or fertile? Biochem Pharmacol. Dec. 1, 2004;68(11):2097-106.
Merriam-Webster Online Dictionary, obtained onlie at: http://www.merriam-webster.com/dictionary/derivative, downloaded 07 Jul. 5, 2008.
U.S. Appl. No. 11/158,724 Office Action Mailed Sep. 17, 2009.
U.S. Appl. No. 11/877,591 Office Action Mailed Feb. 29, 2012.
U.S. Appl. No. 11/877,591 Office Action Mailed Sep. 21, 2012.
U.S. Appl. No. 11/995,685 Office Action Mailed Aug. 20, 2010.
U.S. Appl. No. 11/995,685 Office Action Mailed Nov. 24, 2009.
U.S. Appl. No. 11/995,687 Office Action Mailed Apr. 6, 2012.
U.S. Appl. No. 12/298,459 Office Action Mailed Aug. 10, 2011.
U.S. Appl. No. 12/298,459 Office Action mailed Apr. 6, 2012.
U.S. Appl. No. 12/426,198 Office Action Mailed Feb. 6, 2012.
U.S. Appl. No. 12/426,198 Office Action Mailed Mar. 23, 2011.
U.S. Appl. No. 12/443,959 Office Action Mailed Dec. 13, 2012.
U.S. Appl. No. 12/443,959 Office Action mailed Feb. 15, 2012.
U.S. Appl. No. 12/504,597 Final Office Action Mailed Oct. 3, 2012.
U.S. Appl. No. 12/504,597 Office Action Mailed Dec. 5, 2011.
U.S. Appl. No. 12/522,379 Office Action Mailed Dec. 26, 2012.
U.S. Appl. No. 12/595,848 Office Action Mailed Jan. 13, 2012.
U.S. Appl. No. 12/648,106 Final Office Action Mailed Sep. 25, 2012.
U.S. Appl. No. 12/648,106 Office Action Mailed Jan. 30, 2012.
U.S. Appl. No. 12/729,156 Final Office Action Mailed Oct. 16, 2012.
U.S. Appl. No. 12/729,156 Office Action Mailed Feb. 1, 2012.
U.S. Appl. No. 12/729,580 Office Action Mailed Apr. 10, 2012.
U.S. Appl. No. 12/729,580 Office Action Mailed Jan. 22, 2013.
U.S. Appl. No. 12/729,603 Final Office Action Mailed Oct. 10, 2012.
U.S. Appl. No. 12/729,603 Office Action Mailed Mar. 27, 2012.
U.S. Appl. No. 12/751,902 Office Action Mailed Jul. 13, 2012.
U.S. Appl. No. 12/595,848 Office Action Mailed Mar. 15, 2013.
U.S. Appl. No. 12/738,411 Final Office action Mailed Apr. 11, 2013.
U.S. Appl. No. 12/762,007 Office action Mailed Feb. 11, 2013.
Unger et al., "Poly(ethylene carbonate): A thermoelastic and biodegradable biomaterial for drug eluting stent coatings?" Journal fo Controlled Release, vol. 117, Issue 3, 312-321 (2007).
Verma et al., "Effect of surface properties on nanoparticle-cell interactions," Small 2010, 6, No. 1, 12-21.
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. Controlled release of sirolimus from a multilayered PLGA stent matrix. Biomaterials 2000; 27:5588-95.
Wang et al., "Treatment with melagatran alone or in combination with thrombolytic therapy reduced ischemic brain injury," Exp. Neurol 213(1):171-175 (2008).
Warner et al., "Mitomycin C and airway surgery: how well does it work?" Ontolaryngol Head Neck Surg. 138(6):700-709 (2008).
Wermuth, CG Similarity in drugs: reflections on analogue design. Drug Discov Today. Apr. 2006;11(7-8):348-54.
Witjes et al., "Intravesical pharmacotherapy for non-muscle-invasive bladder cancer: a critical analysis of currently available drugs, treatment schedules, and long-term results," Eur. Urol. 53(1):45-52.
Xu et al., "Biodegradation of poly(l-lactide-co-glycolide tube stents in bile" Polymer Degradation and Stability. 93:811-817 (2008).
PCT/US10/28195 Search Report and Written Opinion mailed Jan. 21, 2011.
PCT/US10/29494 Search Report and Written Opinion mailed Feb. 7, 2011.
PCT/US11/22623 Search Report and Written Opinion mailed Mar. 28, 2011.
PCT/US2011/044263 International Search Report, International Preliminary Report on Patentability and Written Opinion dated Feb. 9, 2012.
PCT/US2007/82775 International Preliminary Report on Patentablity dated Apr. 28, 2009.
PCT/US09/69603 International Search Report mailed Nov. 5, 2010.
PCT/US09/50883 International Preliminary Report on Patentability dated Jan. 18, 2011.
PCT/US10/28253 International Preliminary Report on Patentability dated Sep. 27, 2011.
PCT/US12/33367 International Search Report mailed Aug. 1, 2012.
PCT/US10/42355 International Preliminary Report on Patentability dated Jan. 17, 2012.
PCT/US2011/67921 Search Report and Written Opinion mailed Jun. 22, 2012.
PCT/US2011/051092 International Preliminary Report on Patentability dated Mar. 21, 2013.
PCT/US10/28195 International Preliminary Report on Patentability dated Oct. 6, 2011.
CA 2757276 Office Action dated Feb. 5, 2014.
CA 2794704 Office action dated Feb. 7, 2014.
CA 2667228 Office action dated Jan. 22, 2014.
CA 2679712 Office action dated Feb. 24, 2014.
CA 2667228 office action dated May 7, 2013.
CA 2730995 Office Action dated Feb. 20, 2014.
CA 2756307 Office action dated Mar. 24, 2014.
CA 2756388 Office Action dated Apr. 14, 2014.
CA 2756386 Office action dated May 16, 2014.
CA 2805631 Office Action dated Jan. 17, 2014.
CA 2823355 Office action dated Apr. 14, 2014.
CN 200880007308.1 Office Action dated Jan. 2, 2014.
CN 200880020515 Office Action dated Apr. 15, 2014.
CN 200980136432.2 Office action dated Jul. 3, 2014.
CN 201080024973.9 Office action dated Dec. 20, 2013.
CN 201080024973.9 Office action dated Aug. 7, 2014.

(56) References Cited

OTHER PUBLICATIONS

EP07756094.4 Office Action dated Jan. 21, 2014.
EP10756676.2 Search Report dated Jan. 31, 2014.
EP10800642.0 Search Report dated Mar. 19, 2014.
EP11772624.0 Search Report dated Jun. 5, 2014.
EP09798764.8 Office action dated Jun. 30, 2014.
Han, et al., "Studies of a Novel Human Thrombomodulin Immobilized Substrate: Surface Characterization and Anticoagulation Activity Evaluation." J. Biomater. Sci. Polymer Edn, 2001, 12 (10), 1075-1089.
ID—W00201003529 Office action dated Apr. 28, 2014.
IN-7740/DELNP/2009 Office Action dated Jul. 29, 2014.
JP-2009-545647 Office Action dated Apr. 22, 2014.
JP-2011-518920 Office action dated Oct. 23, 2013.
JP-2013-024508 Office Action dated Apr. 24, 2014.
KR10-2013-7031237 Office action dated Mar. 17, 2014.
Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.
MX/a/2010/01148 Office action dated Feb. 11, 2014.
PCT/US13/41466 International Search Report and Written Opinion dated Oct. 17, 2013.
PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
PCT/US2014/025017 International Search Report and Written Opinion dated Jul. 7, 2014.
Putkisto, K. et al. "Polymer Coating of Paper Using Dry Surface Treatment—Coating Structure and Performance", ePlace newsletter, Apr. 12, 2004, vol. 1, No. 8, pp. 1-20.
U.S. Appl. No. 11/158,724 Office Action Mailed Jun. 25, 2014.
U.S. Appl. No. 11/877,591 Office Action Mailed May 7, 2014.
U.S. Appl. No. 12/426,198 Office Action mailed Feb. 7, 2014.
U.S. Appl. No. 12/504,597 Office Action Mailed Apr. 1, 2014.
U.S. Appl. No. 12/522,379 Office Action Mailed Apr. 8, 2014.
U.S. Appl. No. 12/729,156 Office Action Mailed Feb. 13, 2014.
U.S. Appl. No. 12/729,603 Office Action Mailed Jun. 25, 2014.
U.S. Appl. No. 12/738,411 Office Action mailed Feb. 6, 2014.
U.S. Appl. No. 12/738,411 Office Action mailed May 30, 2014.
U.S. Appl. No. 12/762,007 Final Office action Mailed Apr. 30, 2014.
U.S. Appl. No. 13/086,335 Office action Mailed Apr. 4, 2014.
U.S. Appl. No. 13/445,723 Office action mailed Mar. 14, 2014.
U.S. Appl. No. 13/090,525 Office action mailed Apr. 11, 2014.
U.S. Appl. No. 11/995,685 Office Action Mailed Jun. 18, 2014.

* cited by examiner

POLYMER FILMS FOR MEDICAL DEVICE COATING

RELATED APPLICATIONS

This application claims the benefit of priority to U.S. Provisional Patent Application Ser. No. 60/940,365 filed May 25, 2007 and U.S. Provisional Patent Application Ser. No. 60/979,375 filed Oct. 11, 2007. The disclosure of these applications are incorporated herein by reference in their entirety.

BACKGROUND OF THE INVENTION

Medical devices often must be shielded from interacting with body fluids in vivo. For example, for devices that are electrical in nature, for example, such as pacemakers and other "active" implants for sensing, delivery of therapeutics and/or active control of various bodily functions should be protected.

One prevalent method used to provide this protection is to weld the device inside a titanium or other biocompatible metal "can." Another method to provide the shield necessary to protect a medical device from interaction with bodily fluids in vivo is polymer coating the device. Polymer coating such "active" implants has significant technical challenges and limitations which have made polymer coatings relatively unsuccessful as a means of sealing the devices.

For example, one limitation of traditional coating processes in providing a seal is that traditional polymer coating processes (e.g. dip, spray, etc.) all require the use of a solvent-based system. Exposing the device to a solvent causes problems in the device. Furthermore, there are inherent challenges with effective drying of solvent-based polymer coatings.

Solvent-less coating processes (e.g. vapor deposition, plasma deposition, dry powder coating, etc.) also have limitations in providing seals to active devices. Solvent-less coating processes all require very aggressive conditions that could damage the device—such as elevated temperatures to cure a dry powder coated device.

Additionally, for most current coating technologies, solvent-based and solvent-less, it is often difficult to achieve coatings of uniform thicknesses and prevent the occurrence of defects (e.g. bare spots, webs, pools, clumps). As the size of the substrate decreases, and as the mechanical complexity increases, it grows increasingly difficult to uniformly coat all surfaces of a substrate. Supplemental steps, therefore, are sometimes necessary to assure proper coating, including, for example, multiple coating steps and/or drying between or after the coating steps (in solvent-based systems).

Conventional polymer films likewise have limitations in providing a seal. Conventional polymer films are known to be quite ineffective barriers to the transport of gaseous materials. While this is especially true of small molecule gases, the problem extends to providing a barrier to water vapors and other gases that could deleteriously effect an electrical biomedical implant.

SUMMARY OF THE INVENTION

A cost-effective, easy to apply polymer-based coatings and coating methods to seal a substrate, where the collection process on the substrate is efficient, the coating produced is conformal, substantially defect-free and uniform, and the composition of the coating can be regulated and controlled is provided herein. The method and coatings provide a seal which is impermeable and/or imperveous to gas and/or fluid. The seal can be applied to a variety of substrates, including, but not limited to, implantable medical devices that are electrical in nature such as pacemakers and other "active" implants, which can shield the substrates from interacting with body fluids in vivo.

The present invention relates to coatings and methods for depositing a coating comprising a polymer and a impermeable dispersed solid onto a substrate. Provided herein are novel, easy to apply, polymer-based coatings and coating methods to seal and, thereby, shield, for example, medical devices that are electrical in nature such as pacemakers and other "active" implants from interacting with body fluids in vivo in a manner that disrupts the substrate's (e.g. active medical device's) intended functions and/or proper functioning, if any, or in a manner that has unintended consequences within and/or to the patient. Provided herein are novel, easy to apply, polymer-based coatings and coating methods to seal, for example, implantable medical devices that are electrical in nature such as pacemakers and other "active" implants and, thereby, shield the body from degradation products, leachants, and extractables from the medical device. The coatings and methods provided herein result in a collection process on the substrate that is efficient, a conformal, substantially defect-free, and uniform coating, and a regulatable and controllable coating composition. The coating structures and methods provided herein not only avoid the problems of polymer coatings (solvent-based, and solvent-less), but they also improve the barrier properties of polymer films for use as a seal upon, for example, biologically implanted devices.

Provided herein is a method for electrostatic capture of polymer particles upon a substrate followed by sintering of these particles by exposure to compressed gasses. The coating methods used, including e-RESS, e-SEDS, and/or eDPC are free from elevated temperatures, solvent exposure, plasma environments, and other challenges associated with traditional polymer coating methods.

In some embodiments, a coating comprising electrostatically captured polymer particles (generated by eRESS, eSEDS or eDPC) with either concurrent or sequential captured impermeable particles (by eDFC, eRESS, eSEDS) on a medical implant substrate. A method is also provided for electrostatically capturing polymer particles (generated by eRESS, eSEDS or eDPC) with either concurrent or sequential capturing impermeable particles (by eDPC, eRESS, eSEDS) on a medical implant substrate. Following electrostatic capture of the impermeable particles and the polymer, the method comprises sintering the medical implant substrate with a compressed gas at conditions adequate to cause flow of the polymer particles into a continuous film on the substrate.

The polymers that could be used in the coatings or methods provided herein are all solution or thermally processible polymers (e.g. acrylates, olefins, fluoropolymers, urethanes, etc.). For example, a polymer (or polymers) could be used with known biocompatibility and high resistance to chemical degradation such as polymers of fluorinated olefins. The impermeable particles that could be used in this coating method includes all inorganic particles that can be obtained in the micron and/or sub-micron size range (for example, various compositions of clay, metal-oxides, ceramics, etc.)

In one embodiment, a polymer coating is sufficient to provide the requisite sealing properties. In another embodiment, the coating would contain a polymer continuous phase with particles embedded therein. The existence and distribution of the particles cases an increase in the barrier properties of the film to small molecules and gases by blocking diffusion pathways.

In some embodiments, the surface of the particles is chemically modified to provide greater dispersion and incorporation into the polymer film. In some embodiments of the method for coating, the method comprises chemically modifying the surface of the particles to provide greater dispersion and incorporation into the polymer film. For example in the case of a highly polar particle (e.g. clay, SiO2, TiO2, etc.) in a highly non-polar polymer (e.g. polymeric fluorinated olefins), the process comprises binding or bonding a non-polar chemistry to the surface of the particle prior to incorporation into the powder-coating and sintering process.

Also, provided herein are stacked polymer films with an intervening impermeable layer which could provide similar protection for sensitive devices in vivo without the difficulty associated with welding metal cans around the device. In some embodiments, polymers to be used in the processes and in the coatings provided herein are inherently hydrophobic, thereby greatly reducing the likelihood of penetration of biological fluids. For example, fluoropolymers as a class yield high surface energy surfaces that meet this requirement. However, surfaces created from such polymers in some cases act as membranes through which water vapor transport can occur. Thus, in some embodiments, a second layer that can trap any water vapor that might permeate the fluoropolymer membrane is provided. In some embodiments, the method comprises depositing a hydrophilic polymer layer such as a silicon based polymer over the initial fluoropolymer layer. Silicon based polymers can be designed to possess differing degrees of hydrophilicity and therefore trap any water vapor that might permeate the fluoropolymer layer membrane. In some embodiments, the silicon-based polymer is reduced to native silicon and metallized with titanium. In some embodiments, a third layer of fluoropolymer is deposited to encapsulate the silicon based polymer layer between the fluoropolymer layers. In some embodiments, the coating comprises multiple alternating layers of fluoropolymers and silicon based polymers. In some embodiments, the method comprises alternating multiple layers of the silicon based polymer and the fluoropolymer.

In some embodiments, the coating is designed to remain impermeable and/or impervious to gas and/or fluid for at least as long as the expected life span (e.g., period of time inside a subjects body) of the device and/or substrate it coats.

One aspect of the invention provides methods for depositing a coating comprising a polymer and impermeable dispersed solid on a substrate, comprising discharging at least one impermeable dispersed solid in dry powder form through a first orifice; discharging at least one polymer in dry powder form through a second orifice; depositing the polymer and/or impermeable dispersed solids onto said substrate, wherein an electrical potential is maintained between the substrate and the impermeable dispersed solid and/or polymer particles, thereby forming said coating; and sintering said coating under conditions that do not substantially affect the substrate. In some embodiments, the impermeable dispersed solid is dispersed uniformly on all exposed surfaces of the substrate. In some embodiments, the impermeable dispersed solid is impermeable and/or impervious to gas. In some embodiments, the impermeable dispersed solid is impermeable and/or impervious to fluid. In some embodiments, the impermeable dispersed solid is impermeable and/or impervious to biological material.

In some embodiments, the impermeable dispersed solid comprises nanoparticles, such as, for example, a polyurethane adhesive nanocomposite (organically modified montmorillonite and polyurethane). In some embodiments, the oxygen transmission rate across the coating is at most about 1%, 5%, 10%, 20%, 30%, 40%, 50%, 60%, or 70%. In some embodiments the water vapor permeation through the coating is at most about 1%, 5%, 10%, 20%, 30%, 40%, 50%, 60%, or 70%. In referring to transmission rate or permeation, "about" refers to variations of 0.01% to 0.1%, or 1% to 5%.

Although the size, resistivity and moisture content of the polymer and impermeable dispersed solid may vary widely based on the conditions used, desired particle sizes are typically in the range of 0.01 µm-2500 µm, and more preferably in the range of 0.01 µm-100 µm, resistivity is typically in the range of from about 106 Ωm to about 1024 Ωm and moisture content is less than 5% by weight. In one embodiment of the invention the molecular weight range of the polymer is from about 5,000 a.u. to about 100,000 a.u.

In other embodiments, the first and second orifices are provided as one single orifice wherein the impermeable dispersed solid and polymer may be mixed together prior to discharging. In yet other embodiments the impermeable dispersed solid and polymer particles may be discharged simultaneously or in succession. In another embodiment of the invention the method further comprises discharging a third dry powder comprising a second impermeable dispersed solid whereby a coating comprising at least two different impermeable dispersed solids is deposited on said substrate. In certain other embodiments of the invention the impermeable dispersed solid is prepared by milling, jet-milling, granulation, spray drying, crystallizing or fluidizing.

In a further embodiment the impermeable dispersed solid and/or the polymer becomes electrostatically charged prior to deposition, and the substrate may be electrically grounded. In a preferred embodiment, the substrate is electrostatically charged. In some embodiments the polymer and impermeable dispersed solid are discharged using a gas based propellant, which typically comprises carbon dioxide, nitrous oxide, hydrofluorocarbons, chlorofluorocarbons, helium, nitrogen, compressed air, argon, or volatile hydrocarbons with a vapor pressure greater than 750 Torr at 20° C., and is preferably carbon dioxide.

In one embodiment of the invention the impermeable dispersed solid comprises at least one drug. In another embodiment of the invention the ratio of impermeable dispersed solid to polymer is from about 1:1000 to about 3:10. In some embodiments, the amount of impermeable dispersed solid will depend on the particular dispersed solid being employed, the type of substrate, and the medical condition being treated.

Yet another aspect of the invention provides methods for depositing a coating comprising a polymer and a impermeable dispersed solid on a substrate, comprising discharging at least one impermeable dispersed solid in a therapeutically desirable morphology in dry powder form through a first orifice; forming a supercritical or near supercritical fluid mixture that includes at least one supercritical fluid solvent and at least one polymer and discharging said supercritical or near supercritical fluid solution through a second orifice under conditions sufficient to form solid particles of the polymer; depositing the polymer and/or impermeable dispersed solids onto said substrate, wherein an electrical potential is maintained between the substrate and the impermeable dispersed solids and/or polymer particles, thereby forming said coating and sintering said coating under conditions that do not substantially disrupt the substrate's (e.g. active medical device's) intended functions and proper functioning, if any, or that have unintended consequences within and/or to the patient once implanted.

Each of the above methods may be carried out from about 0° C. to about 80° C. and from about 0.1 atmospheres to about 73 atmospheres, in either open or closed vessel. In some embodiments, the substrate is a biomedical implant which may be a. a stent (e.g., vascular stents), electrode, catheter, lead, implantable pacemaker, implantable cardioverter, a housing for an implantable pacemaker, a housing for an implantable defibrillator, a housing for an implantable cardioverter, sensor, drug delivery device, therapy delivery device, device comprising telemetry capability, device comprising electrical impulses, diagnostic device, measurement device, joint, screw, rod, ophthalmic implant, femoral pin, bone plate, graft, anastomotic device, perivascular wrap, suture, staple, shuntsfor hydrocephalus, dialysis graft, colostomy bag attachment device, ear drainage tube, lead for pace makers and implantable cardioverters and defibrillators, vertebral disk, bone pin, suture anchor, hemostatic barrier, clamp, screws, plate, clip, vascular implant, tissue adhesive, sealant, tissue scaffolds, shunts, opthalmic implant, prosthetic, shunt, urologic implant, reproductive anatomy device, gastrologic device, neurologic lead, neurologic device, various types of dressings (e.g., wound dressings), bone substitutes, intraluminal devices, and vascular supports.

In some embodiments of the invention the thickness of said coating is from about 1 to about 100 μm, preferably about 10 μm, and the variation in the thickness along said coating is within 0.5 μm, within 0.25 μm, within 0.1 μm or within 10% of the total thickness of said coating, within 5% of the total thickness of said coating, or within 2.5% of the total thickness of said coating. In yet other embodiments, the impermeable dispersed solid is positioned at a selected distance from top of said coating. In further embodiments, the impermeable dispersed solid is positioned at about midway between the top of said coating and the substrate surface. In other embodiments of the invention the variability in the amount of impermeable dispersed solid deposited on said substrate is 20% or less, 15% or less, 10% or less, 5% or less, for a batch of substrates coated at the same time. Preferably the variability is 5% or less.

In yet other embodiments of the invention, the methods further comprise depositing a top layer on said coating wherein said top layer is a polymer film. In some embodiments, the polymer film has a thickness of 0.5 to 10 microns, and can be deposited by an eRESS or eSEDS, or a eDPC process. In yet other embodiments, the polymer film is formed by depositing a single polymer and for example by depositing substantially pure PBMA.

The invention further relates to the use of a supercritical solution comprising a second fluid in its supercritical state.

In some embodiments, the addition of a second fluid in its supercritical state is to act as a flammability suppressor. In other embodiments, a second fluid is used, wherein said second fluid has critical parameters lower than the first fluid's critical parameters, and therefore lowers the critical properties of the mixture/solution enabling access to the mixture supercritical state.

In some embodiments the supercritical solution comprises isobutylene. In other embodiments, the supercritical fluid comprises isobutylene and carbon dioxide as a second fluid.

Other embodiments of the invention provide a way to dissolve two polymers in a supercritical solvent. In some embodiments said two polymers are PEVA and PBMA. In other embodiments, a supercritical solution comprising two polymers is used to create a RESS spray of the polymers generating ~10 to 100 nm particles of each polymer. In further embodiments, PEVA and PBMA are dissolved in a supercritical solvent that further comprises $CO_2$ to act as a fire suppressor in the event of an ignition source causing a fire.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended Claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
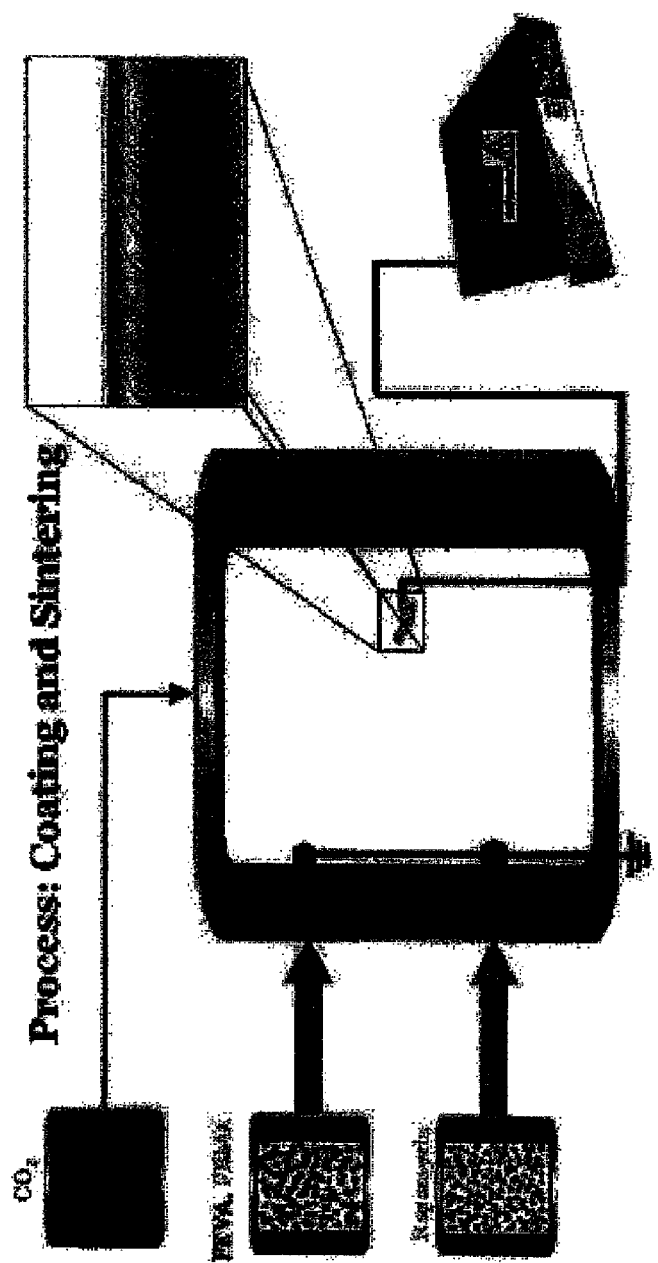
FIG. 1. Schematic Representation of the Coating and Sintering Process Apparatus.
Figure 2:
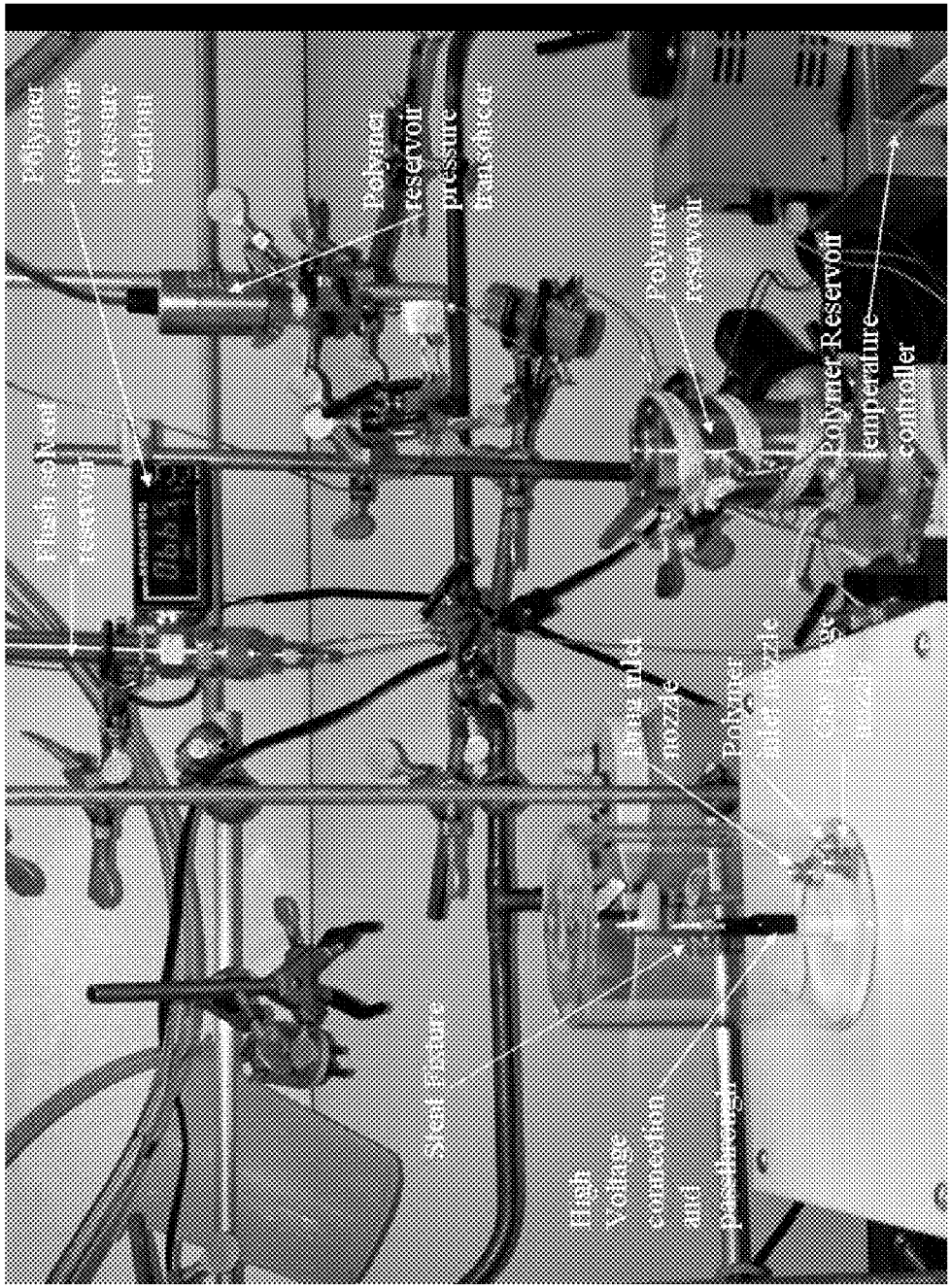
FIG. 2. Detailed images of the Coating and Sintering Process Apparatus.
Figure 2:
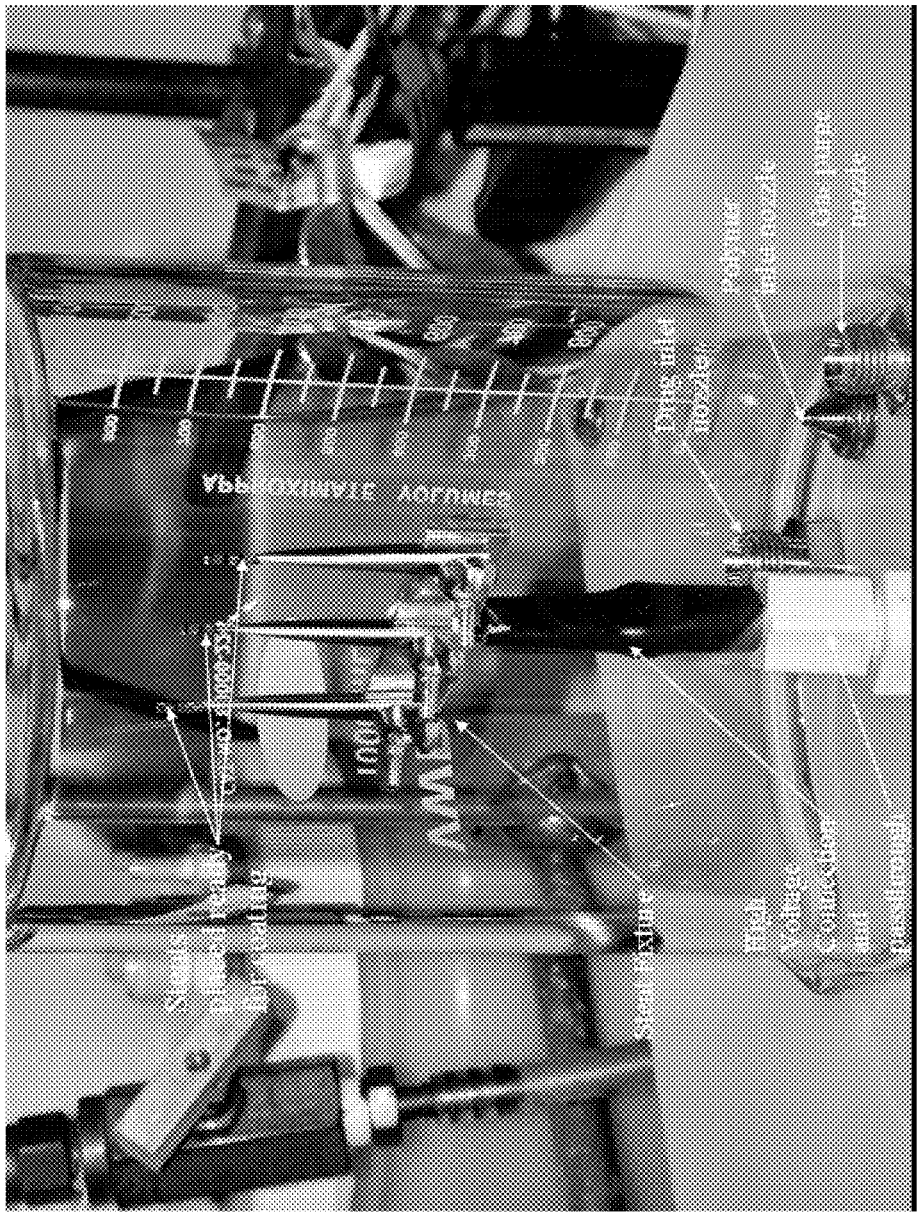
Figure 2:
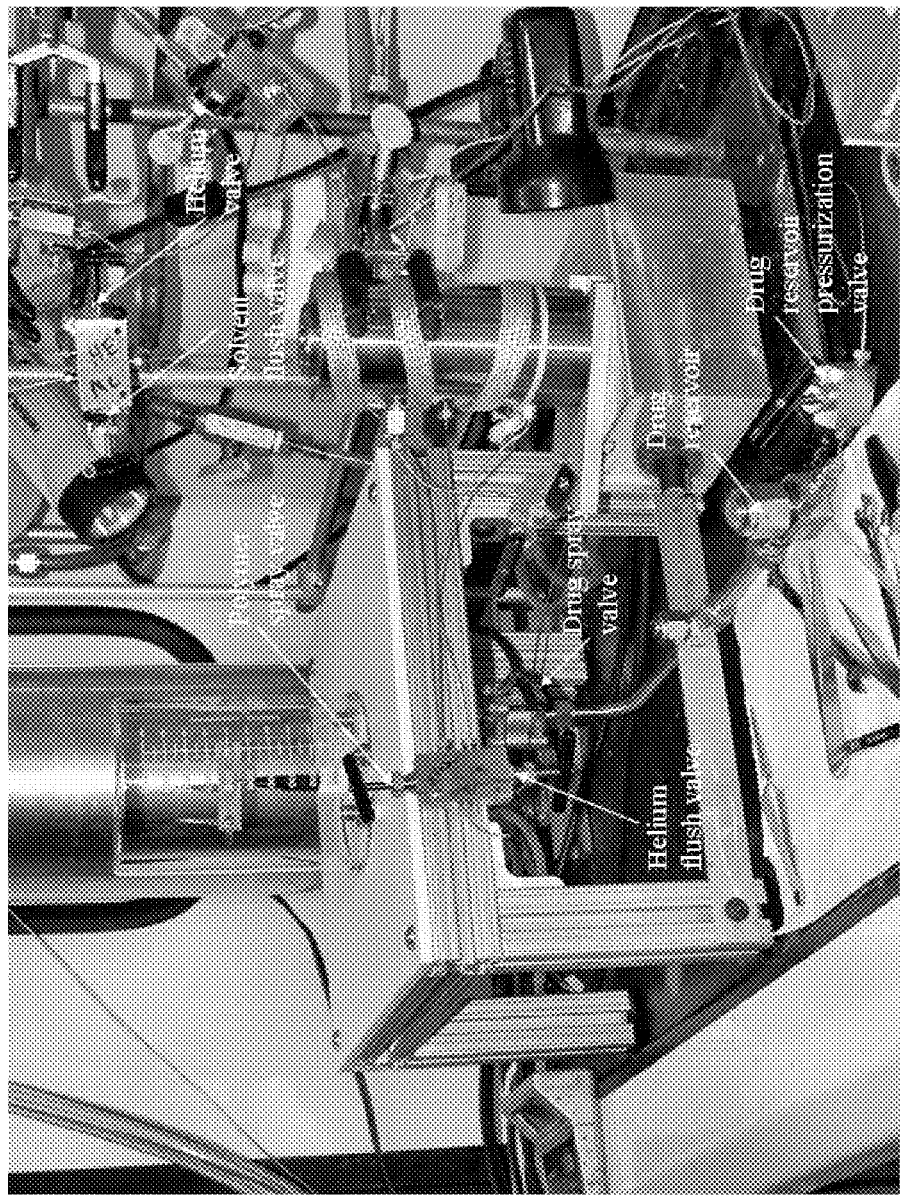

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Applicants specifically intend that all United States patent references cited herein be incorporated herein by reference in their entirety.

The present invention relates to coatings and methods for depositing a coating comprising a polymer and a impermeable dispersed solid onto a substrate. Provided herein are novel, easy to apply, polymer-based coatings and coating methods to seal and, thereby, shield, for example, implantable medical devices that are electrical in nature such as pacemakers and other "active" implants from interacting with body fluids in vivo in a manner that disrupts the medical device's intended functions and proper functioning, or in a manner that has unintended consequences within and/or to the patient. Provided herein are novel, easy to apply, polymer-based coatings and coating methods to seal, for example, implantable medical devices that are electrical in nature such as pacemakers and other "active" implants and, thereby, shield the body from degradation products, leachants, extractables from the medical device. The coatings and methods provided herein result in a collection process on the substrate that is an efficient, conformal, substantially defect-free, and uniform coating, and a regulatable and controllable coating composition. The coating structures and methods provided herein not only avoid the problems of polymer coatings (solvent-based, and solvent-less), but they also improve the barrier properties of polymer films for use as a seal upon, for example, biologically implanted devices.

Provided herein is a composite material coating containing polymer to provide increased barrier properties for gases such as water vapor, and method of creating such coating.

Provided herein is a composite material coating containing polymer plus a impermeable dispersed solid to provide increased barrier properties for gases such as water vapor, and method of creating such coating.

Provided herein is the a method for electrostatic capture of polymer particles upon a substrate followed by sintering of these particles by exposure to compressed gasses. The coating methods used, including e-RESS, e-SEDS, and/or eDPC are free from elevated temperatures, solvent exposure, plasma environments, and other challenges associated with traditional polymer coating methods.

In some embodiments, a coating comprising electrostatically captured polymer particles (generated by eRESS, eSEDS or eDPC) alone or optionally with either concurrent or sequential captured impermeable particles (by eDPC, eRESS, eSEDS) on a medical implant substrate. A method is also provided for electrostatically capturing polymer particles (generated by eRESS, eSEDS or eDPC) alone or with either concurrent or sequential capturing impermeable particles (by eDPC, eRESS, eSEDS) on a medical implant substrate. Following electrostatic capture of the polymer and optionally impermeable particles, the method comprises sintering the medical implant substrate with a compressed gas at conditions adequate to cause flow of the polymer particles into a continuous film on the substrate.

The polymers that could be used in the coatings or methods provided herein are all solution or thermally processible polymers (e.g. acrylates, olefins, fluoropolymers, urethanes, etc.). For example, a polymer (or polymers) could be used with known biocompatibility and high resistance to chemical degradation such as polymers of fluorinated olefins. The impermeable particles that could be used in this coating method includes all inorganic particles that can be obtained in the micron and/or sub-micron size range. For example various compositions of clay, metal-oxides, ceramics, etc.

The resulting film would contain a polymer continuous phase optionally with particles embedded therein. The existence and distribution of the particles causes an increase in the barrier properties of the film to small molecules and gases by blocking diffusion pathways.

In some embodiments of the coating, the surface of the particles is chemically modified to provide greater dispersion and incorporation into the polymer film. In some embodiments of the method for coating, the method comprises chemically modifying the surface of the particles to provide greater dispersion and incorporation into the polymer film. For example in the case of a highly polar particle (e.g. clay, $SiO_2$, $TiO_2$, etc.) in a highly non-polar polymer (e.g. polymeric fluorinated olefins), the process comprises binding or bonding a non-polar chemistry to the surface of the particle prior to incorporation into the powder-coating and sintering process.

Provided herein are stacked polymer films with an intervening impermeable layer which could provide similar protection for sensitive devices in vivo without the difficulty associated with welding metal cans around the device. In some embodiments, polymers to be used in the processes and in the coatings provided herein are inherently hydrophobic, thereby greatly reducing the likelihood of penetration of biological fluids. For example, fluoropolymers as a class yield high surface energy surfaces that meet this requirement. However, surfaces created from such polymers in some cases act as membranes through which water vapor transport can occur. Thus, in some embodiments, a second layer that can trap any water vapor that might permeate the fluoropolymer membrane is provided. In some embodiments, the method comprises depositing a hydrophilic polymer layer such as a silicon based polymer over the initial fluoropolymer layer. Silicon based polymers can be designed to possess differing degrees of hydrophilicity and therefore trap any water vapor that might permeate the fluoropolymer layer membrane. In some embodiments, the silicon-based polymer is reduced to native silicon and metallized with titanium.

In some embodiments, a highly absorbent material is used as the water-vapor trapping material. In some embodiments, the highly absorbent material comprises a hydrophilic polymer. In some embodiments, highly absorbent material comprises a superabsorbent polymer.

In some embodiments, a third layer of fluoropolymer is deposited to encapsulate the silicon based polymer layer between the fluoropolymer layers. In some embodiments, the coating comprises multiple alternating layers of fluoropolymers and silicon based polymers. In some embodiments, the method comprises alternating multiple layers of the silicon based polymer and the fluoropolymer.

In some embodiments, the coating is designed to remain impermeable for at least as long as the expected life span of the device and/or substrate it coats.

One aspect of the invention provides methods for depositing a coating comprising a polymer and impermeable dispersed solid on a substrate, comprising discharging at least one impermeable dispersed solid in dry powder form through a first orifice; discharging at least one polymer in dry powder form through a second orifice; depositing the polymer and/or impermeable dispersed solids onto said substrate, wherein an electrical potential is maintained between the substrate and the impermeable dispersed solid and/or polymer particles, thereby forming said coating; and sintering said coating under conditions that do not substantially affect the substrate. In some embodiments, the impermeable dispersed solid is dispersed uniformly on all exposed surfaces of the substrate.

In some embodiments, the impermeable dispersed solid comprises a nanoparticle, such as, for example, a polyurethane adhesive nanocomposite (organically modified montmorillonite and polyurethane). In some embodiments, the oxygen transmission rate across the coating is at most about 1%, 5%, 10%, 20%, 30%, 40%, 50%, 60%, or 70%. In some embodiments the water vapor permeation through the coating is at most about 1%, 5%, 10%, 20%, 30%, 40%, 50%, 60%, or 70%. In referring to transmission rate or permeation, "about" refers to variations of 0.01% to 0.1%, or 1% to 5%.

In some embodiments, the impermeable dispersed solid comprises a nanoparticle that is impervious to small particle transport. In some embodiments, the nanoparticle comprises at least one of a ceramic and a metal. In some embodiments, the nanoparticle comprises clay. In some embodiments the nanoparticle comprises silica. In some embodiments, the nanoparticle comprises titanium oxide. In some embodiments, the nanoparticle does not include nickel. In some embodiments, the nanoparticle does not include copper. In some embodiments, the small particle transmission rate across the coating is at most about 0.001%, 0.01%, 0.1%, 1%, 5%, 10%, 20%, 30%, 40%, 50%, 60%, or 70%. In some embodiments, the oxygen transmission rate across the coating is at most about 0.001%, 0.01%, 0.1%, 1%, 5%, 10%, 20%, 30%, 40%, 50%, 60%, or 70%. In some embodiments the water vapor permeation through the coating is at most about 0.001%, 0.01%, 0.1%, 1%, 5%, 10%, 20%, 30%, 40%, 50%, 60%, or 70%. In referring to transmission rate or permeation, "about" refers to variations of 0.001% to 0.01%, 0.01% to 0.1%, or 1% to 5%.

Although the size, resistivity and moisture content of the polymer and impermeable dispersed solid may vary widely based on the conditions used, desired particle sizes are typically in the range of 0.01 μm-2500 μm, and more preferably in the range of 0.01 μm-100 μm, resistivity is typically in the range of from about 106 Ωm to about 1024 Ωm and moisture content is less than 5% by weight. In one embodiment of the invention the molecular weight range of the polymer is from about 5,000 a.u. to about 100,000 a.u.

In other embodiments, the first and second orifices are provided as one single orifice wherein the impermeable dispersed solid and polymer may be mixed together prior to discharging. In yet other embodiments the impermeable dispersed solid and polymer particles may be discharged simultaneously or in succession. In another embodiment of the invention the method further comprises discharging a third thy powder comprising a second impermeable dispersed solid whereby a coating comprising at least two different impermeable dispersed solids is deposited on said substrate. In certain other embodiments of the invention the impermeable dispersed solid is prepared by milling, jet-milling, granulation, spray drying, crystallizing or fluidizing.

In a further embodiment the impermeable dispersed solid and/or the polymer becomes electrostatically charged prior to deposition, and the substrate may be electrically grounded. In a preferred embodiment, the substrate is electrostatically charged. In some embodiments the polymer and impermeable dispersed solid are discharged using a gas based propellant, which typically comprises carbon dioxide, nitrous oxide, hydrofluorocarbons, chlorofluorocarbons, helium, nitrogen, compressed air, argon, or volatile hydrocarbons with a vapor pressure greater than 750 Torr at 20° C., and is preferably carbon dioxide.

In one embodiment of the invention the impermeable dispersed solid comprises at least one drug. In another embodiment of the invention the ratio of impermeable dispersed solid to polymer is from about 1:1000 to about 3:10. In some embodiments, the amount of impermeable dispersed solid will depend on the particular dispersed solid being employed, the type of substrate, and the medical condition being treated.

Yet another aspect of the invention provides methods for depositing a coating comprising a polymer and a impermeable dispersed solid on a substrate, comprising discharging at least one a impermeable dispersed solid in a therapeutically desirable morphology in dry powder form through a first orifice; forming a supercritical or near supercritical fluid mixture that includes at least one supercritical fluid solvent and at least one polymer and discharging said supercritical or near supercritical fluid solution through a second orifice under conditions sufficient to form solid particles of the polymer; depositing the polymer and/or impermeable dispersed solids onto said substrate, wherein an electrical potential is maintained between the substrate and the impermeable dispersed solids and/or polymer particles, thereby forming said coating and sintering said coating under conditions that do not substantially disrupt the substrate's (e.g. implantable active medical device's) intended functions and proper functioning, if any, or that have unintended consequences within and/or to the patient once implanted.

Each of the above methods may be carried out from about 0° C. to about 80° C. and from about 0.1 atmospheres to about 73 atmospheres, in either open or closed vessel. In some embodiments, the substrate is a stent (e.g., vascular stents), electrode, catheter, lead, implantable pacemaker, implantable cardioverter, a housing for an implantable pacemaker, a housing for an implantable defibrillator, a housing for an implantable cardioverter, sensor, drug delivery device, therapy delivery device, device comprising telemetry capability, device comprising electrical impulses, diagnostic device, measurement device, joint, screw, rod, ophthalmic implant, femoral pin, bone plate, graft, anastomotic device, perivascular wrap, suture, staple, shunts for hydrocephalus, dialysis graft, colostomy bag attachment device, ear drainage tube, lead for pace makers and implantable cardioverters and defibrillators, vertebral disk, bone pin, suture anchor, hemostatic barrier, clamp, screws, plate, clip, vascular implant, tissue adhesive, sealant, tissue scaffolds, shunts, opthalmic implant, prosthetic, shunt, urologic implant, reproductive anatomy device, gastrologic device, neurologic lead, neurologic device, various types of dressings (e.g., wound dressings), bone substitutes, intraluminal devices, and vascular supports.

In some embodiments of the invention the thickness of said coating is from about 1 to about 100 µm, preferably about 10 µm, and the variation in the thickness along said coating is within 0.5 µm, within 0.25 µm, within 0.1 µm or within 10% of the total thickness of said coating, within 5% of the total thickness of said coating, or within 2.5% of the total thickness of said coating. In yet other embodiments, the impermeable dispersed solid is positioned at a selected distance from top of said coating. In further embodiments, the impermeable dispersed solid is positioned at about midway between the top of said coating and the substrate surface. In other embodiments of the invention the variability in the amount of impermeable dispersed solid deposited on said substrate is 20% or less, 15% or less, 10% or less, 5% or less, for a batch of substrates coated at the same time. Preferably the variability is 5% or less.

In yet other embodiments of the invention, the methods further comprise depositing a top layer on said coating wherein said top layer is a polymer film. In some embodiments, the polymer film has a thickness of 0.5 to 10 microns, and can be deposited by an eRESS or eSEDS, or a eDPC process. In yet other embodiments, the polymer film is formed by depositing a single polymer and can be formed by depositing substantially pure PBMA.

The invention further relates to the use of a supercritical solution comprising a second fluid in its supercritical state.

In some embodiments, the addition of a second fluid in its supercritical state is to act as a flammability suppressor. In other embodiments, a second fluid is used, wherein said second fluid has critical parameters lower than the first fluid's critical parameters, and therefore lowers the critical properties of the mixture/solution enabling access to the mixture supercritical state.

In some embodiments the supercritical solution comprises isobutylene. In other embodiments, the supercritical fluid comprises isobutylene and carbon dioxide as a second fluid.

Other embodiments of the invention provide a way to dissolve two polymers in a supercritical solvent. In some embodiments said two polymers are PEVA and PBMA. In other embodiments, a supercritical solution comprising two polymers is used to create a RESS spray of the polymers generating ~10 to 100 nm particles of each polymer. In further embodiments, PEVA and PBMA are dissolved in a supercritical solvent that further comprises $CO_2$ to act as a fire suppressor in the event of an ignition source causing a fire.

One aspect of the invention entails the deposition of the a impermeable dispersed solid as dry powders, using electrostatic capture to attract the powder particles to the substrate. Dry powder spraying is well known in the art, and dry powder spraying coupled with electrostatic capture has been described, for example in U.S. Pat. No. 5,470,603 6,319,541 or 6,372,246. The deposition of the polymer can be performed in any number of standard procedures, as the morphology of the polymer, so long as it provides coatings possessing the desired properties (e.g. thickness, conformity, defect-free, uniformity), and are free from elevated temperatures, solvent exposure, plasma environments, and other challenges associated with traditional polymer coating methods.

The second step of the coating process involves taking the substrates that have been coated with impermeable dispersed solids and polymers and subjecting them to a sintering process that takes place under conditions free from elevated temperatures, solvent exposure, plasma environments, and other challenges associated with traditional polymer coating methods. The sintering process as used in the current invention refers to the process by which the co-deposited impermeable dispersed solid—polymer matrix become fused and adherent to the substrate by treatment of the coated substrate with a compressed gas, compressed liquid, or supercritical fluid that is a non-solvent for the polymers and the impermeable dispersed solid(s), but a plasticizing agent for the polymer. The sintering process takes place under conditions (e.g. mild temperatures), and using benign fluids (e.g. supercritical carbon dioxide) which will not affect the active substrate or its subsequent function, if any.

One aspect of the invention is the combination of two or more of the e-DPC, e-RESS and e-SEDS spraying techniques.

A specific aspect of the invention involves the dry powder spraying of impermeable dispersed solid, in a preferred particle size, into the same capture vessel as a polymer that is also dry powder sprayed, whereby the spraying of the impermeable dispersed solid and the polymer is sequential or simultaneous.

In some embodiments, the invention involves the e-DPC spraying of the impermeable dispersed solid, into the same capture vessel as a polymer that is sequentially or simultaneously sprayed by the eRESS spray process. In some embodiments, the invention involves the e-DPC spraying of the impermeable dispersed solid, into the same capture vessel as a polymer that is sequentially or simultaneously sprayed by the eSEDS spray process. In some embodiments, the invention involves the e-DPC spraying of the impermeable dispersed solid, into the same capture vessel as a polymer that is sequentially or simultaneously sprayed by the eDPC spray process.

In some embodiments, the invention involves the e-RESS spraying of the impermeable dispersed solid, into the same capture vessel as a polymer that is sequentially or simultaneously sprayed by the eRESS spray process. In some embodiments, the invention involves the e-RESS spraying of the impermeable dispersed solid, into the same capture vessel as a polymer that is sequentially or simultaneously sprayed by the eSEDS spray process. In some embodiments, the invention involves the e-RESS spraying of the impermeable dispersed solid, into the same capture vessel as a polymer that is sequentially or simultaneously sprayed by the eDPC spray process.

In some embodiments, the invention involves the e-SEDS spraying of the impermeable dispersed solid, into the same capture vessel as a polymer that is sequentially or simultaneously sprayed by the eRESS spray process. In some embodiments, the invention involves the e-SEDS spraying of the impermeable dispersed solid, into the same capture vessel as a polymer that is sequentially or simultaneously sprayed by the eSEDS spray process. In some embodiments, the invention involves the e-SEDS spraying of the impermeable dispersed solid, into the same capture vessel as a polymer that is sequentially or simultaneously sprayed by the eDPC spray process.

Any combination of the above processes is contemplated by this aspect of the invention.

In further aspects of the invention the substrates that have been coated with impermeable dispersed solid and polymers, as described in the above embodiments are then subjected to a sintering process. The sintering process takes place under conditions free from elevated temperatures, solvent exposure, plasma environments, and other challenges associated with traditional polymer coating methods, and refers to a process by which the co-deposited impermeable dispersed solid-polymer matrix, becomes fused and adherent to the substrate. This is achieved by treating the coated substrate with a compressed gas, compressed liquid or supercritical fluid that is a non-solvent for the polymers, the impermeable dispersed solids, but a plasticizing agent for the polymer. The sintering process takes place under conditions (e.g. mild temperatures), and using benign fluids (e.g. supercritical carbon dioxide) which will not affect the active substrate or its subsequent function, if any. Other sintering processes, which do not affect the active substrate or its subsequent function, if any may also be contemplated by the present invention.

DEFINITIONS

As used in the present specification, the following words and phrases are generally intended to have the meanings as set forth below, except to the extent that the context in which they are used indicates otherwise.

"Substrate" as used herein, refers to any surface upon which it is desirable to deposit a coating comprising a polymer or a mix of polymer with or without impermeable dispersed solid, or hydrophobic polymers and a water-vapor-trapping material, wherein the coating process does not substantially disrupt the substrate's (e.g. implantable active medical device's) intended functions and/or proper functioning, if any, or in a manner that has unintended consequences within and/or to the patient. Biomedical implants are of particular interest for the present invention; however the present invention is not intended to be restricted to this class of substrates. Those of skill in the art will appreciate alternate substrates that could benefit from the coating process described herein, such as temporary implantable devices, diagnostic tests or kits.

"Biomedical implant" as used herein refers to any implant for insertion into the body of a human or animal subject, including but not limited to a stent (e.g., vascular stents), electrode, catheter, lead, implantable pacemaker, implantable cardioverter, a housing for an implantable pacemaker, a housing for an implantable defibrillator, a housing for an implantable cardioverter, sensor, drug delivery device, therapy delivery device, device comprising telemetry capability, device comprising electrical impulses, diagnostic device, measurement device, joint, screw, rod, ophthalmic implant, femoral pin, bone plate, graft, anastomotic device, perivascular wrap, suture, staple, shuntsfor hydrocephalus, dialysis graft, colostomy bag attachment device, ear drainage tube, lead for pace makers and implantable cardioverters and defibrillators, vertebral disk, bone pin, suture anchor, hemostatic barrier, clamp, screws, plate, clip, vascular implant, tissue adhesive, sealant, tissue scaffolds, shunts, opthalmic implant, prosthetic, shunt, urologic implant, reproductive anatomy device, gastrologic device, neurologic lead, neurologic device, various types of dressings (e.g., wound dressings), bone substitutes, intraluminal devices, and vascular supports, etc.

The implants may be formed from any suitable material, including but not limited to organic polymers (including stable or inert polymers and biodegradable polymers), metals, inorganic materials such as silicon, and composites thereof, including layered structures with a core of one material and one or more coatings of a different material.

Subjects into which biomedical implants of the invention may be applied or inserted include both human subjects (including male and female subjects and infant, juvenile, adolescent, adult and geriatric subjects) as well as animal subjects (including but not limited to dog, cat, horse, monkey, etc.) for veterinary purposes.

In a preferred embodiment the biomedical implant is an implantable pacemaker, cardioverter or defibrillator, or another active device or any implantable (permanent or temporary) device requiring sealing to prevent gas or fluid permeation.

"Active" or "Active medical device" as used herein refers to medical devices that are electrical in nature, such as pacemakers and other medical devices for sensing, delivery of therapeutics and/or active control of various bodily functions.

"Medical device" as used herein can refer to biological implants as defined herein active or inactive. A medical device may be permanently implantable, temporarily implantable, entirely implantable (such as, for example, an implantable defibrillator), partially implantable (such as, for example, a sensing drainage catheter) and/or can refer to devices used on or in a patient during a diagnostic or therapeutic procedure, including during an invasive surgery or during a minimally invasive surgery. A medical device includes any instrument, apparatus, appliance, material or other article, whether used alone or in combination, including any software necessary for its proper application intended by the manufacturer to be used for human beings for the purpose of: diagnosis, prevention, monitoring, treatment or alleviation of disease, alleviation of pain, diagnosis, monitoring, treatment, alleviation of or compensation for an injury or handicap, investigation, replacement or modification of the anatomy or of a physiological process, control of conception, and which does not achieve its principal intended action in or on the human body by pharmacological, immunological or metabolic means, but which may be assisted in its function by such means. For example, an insulin pump implanted in a diabetic person which dispenses insulin stored in the pump into the patient's blood based upon glucose levels sensed by the pump is a medical device (and is an active medical device and a biological implant).

"Biological material" as used herein can refer a biological material in gas or fluid state including small solid particles.

"Defect" as used herein can refer to, but is not limited to: surface topology variability, such as a clump, a web, or a pool; a through-layer deficiency, such as a bare spot, a fracture, a crack, a pin hole, a thin spot, a blemish; or a under-layer defect, such as a bubble between layers, a bubble beneath a layer, matter trapped beneath a layer or between layers of coating which is not a part of the substrate or of the layer(s), such as dust, liquid, gas, or particulate, An under-layer defect might affect the seal of a substrate device. For example, an under-layer water vapor bubble might act as a sink for diffusion of water vapor, making an active device more prone to interacting with the vapor and/or potentially with body fluids in vivo in a manner that disrupts the substrate's (e.g. active device's) intended functions and/or proper functioning, if any, or in a manner that has unintended consequences within and/or to the patient. Likewise, any other defect (through-layer, or surface topology variability) which allows gas or fluids to interact with the substrate can potentially result in disruption of the substrate's (e.g. active device's) intended functions and/or proper functioning, if any, or in a manner that has unintended consequences within and/or to the patient (such as, for a non-limiting example, freeing leachables, and/or creating or releasing degradation products or extractables from the device and into the body of the patient).

"Conformal coating", "conformally coated", or "conformably coated" as used herein can refer to a protective covering that conforms to the configuration of the objects coated. A covering that is conformal covers susbtantially all surfaces with a uniform layer. For example, a coating layering process may confomally coat a device with a 10 micron coating (of a layer or of layers) plus or minus 10%, which results in a 10 micron plus or minus 10% coating on every external surface of the device that is at least about 20 microns apart from another external surface of the device (external surfaces of the device that are closer may appear to have thicker coatings as the coatings on of the two nearby surfaces join).

"Seal" or "Substantially seal" as used herein can refer to coating that substantially shields a substrate from interacting with materials (fluids, gases, solids), in a manner that disrupts the substrate's intended functions and/or proper functioning, if any, or in a manner that has unintended consequences within and/or to the patient. As used herein, the term(s) can refer to coating that substantially shields transmission of degradation products, leachants, and extractables from the substrate past and/or through the coating. Seals on a substrate can be applied to electronic circuitry to act as protection for the circuitry against, for example, moisture, dust, chemicals, and/or temperature extremes. Similarly, seals can be applied to devices to act as protection against, for example, moisture, dust, chemicals, leachants, extractable components (extractables) and/or degradation products, from passing from the device through the coating layer(s). A seal, therefore can be a one-way and/or two-way barrier to moisture, dust, chemicals, leachants, degradation products, and/or other material (fluid or gas), including biologic material. The one-way barrier can be a barrier in either direction, a barrier to allowing material to contact the substrate, or a barrier to allowing material to pass from the substrate through the coating for example to the blood stream of a subject. For example, a medical device that is electrical in nature such as a pacemaker and/or another "active" implant body fluids in vivo can be substantially sealed by a coating and, thereby, substantially shielded from interacting with materials (fluids, gases, solids), in a manner that disrupts the substrate's intended functions and/or proper functioning, if any, or in a manner that has unintended consequences within and/or to the patient. Medical devices that are not electrical in nature (or not primarily electrical in nature) may also be sealed as provided herein. "Substantially" where used herein with respect to sealing or seals, can mean at least about one of 85%, 90%, 95%, 96%, 97%, 98%, 99%, 99.5% 99.6%, 99.7%, 99.8%, 99.9%, 99.95%, 99.99%, and 99.995% sealed. "About" where used herein with respect to sealing or seals percentages, can mean variability of 0.1 to 0.5%, or 1-5%. "Substantially" where used herein with respect to sealing or seals, can also or alternatively mean a seal that passes a coating visual inspection, an adhesion test, a chemical resistance test, and/or a coating fatigue test, device fatigue in an in vitro test, device fatigue in a simulated in vivo environment test, a resistance test in a simulated in vivo environment Examples of such tests include, but are not limited to, ASTM D6677, ASTM D3359, ASTM D4541, ASTM D2197, ASTM D2370, ASTM D5179, ASTM D4145, ASTM 4146, ASTM F1854-01.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds. Examples of ploymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, polyurethanes, polystyrenes, copolymers, silicones, polyorthoesters, polyanhydrides, copolymers of vinyl monomers, polycarbonates, polyethylenes, polypropylenes, polylactic acids, polyglycolic acids, polycaprolactones, polyhydroxybutyrate valerates, polyacrylamides, polyethers, polyurethane dispersions, polyacrylates, acrylic latex dispersions, polyacrylic acid, mixtures and copolymers thereof. The polymers of the present invention may be natural or synthetic in origin, including gelatin, chitosan, dextrin, cyclodextrin, Poly(urethanes), Poly(siloxanes) or silicones, Poly(acrylates) such as poly(methyl methacrylate), poly(butyl methacrylate), and Poly(2-hydroxy ethyl methacrylate), Poly(vinyl alcohol) Poly(olefins) such as poly(ethylene), poly(isoprene), halogenated polymers such as Poly(tetrafluoroethylene)—and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc. Suitable polymers also include absorbable and/or resorbable polymers including the following, combinations, copolymers and derivatives of the following: Polylactides (PLA), Polyglycolides (PGA), Poly(lactide-co-glycolides) (PLGA), Polyanhydrides, Polyorthoesters, Poly(N-(2-hydroxypropyl) methacrylamide), Poly(1-aspartamide), etc.

"Water-vapor trapping material" as used herein includes, but is not limited to a hydrophilic polymer. "Water-vapor trapping material" as used herein includes, but is not limited to a highly absorbent material, which may comprises a superabsorbent polymer. Examples of water-vapor trapping materials include, but are not limited to, acrylate polymers, generally formed from acrylic acid, methacrylic acid, acrylate, methyl acrylate, ethyl acrylate, methyl methacrylate, ethyl methacrylate, a dialkylaminoalkyl acrylate, a dialkylaminoalkyl methacrylate, a trialkylammonioalkyl acrylate, and/or a trialkylammonioalkyl methacrylate, and include the polymers or copolymers of acrylic acid, methacrylic acid, methyl methacrylate, ethyl methacrylate, 2-dimethylaminoethyl methacrylate, and trimethylammonioethyl methacrylate chloride. Examples of hydrophilic polymers include, but is not limited to poly(N-vinyl lactams), poly(N-vinyl acrylamides), poly(N-alkylacrylamides), substituted and unsubstituted acrylic and methacrylic acid polymers, polyvinyl alcohol (PVA), polyvinylamine, copolymers thereof and copolymers with other types of hydrophilic monomers (e.g. vinyl acetate), polysaccharides, crosslinked acrylate polymers and copolymers, carbomers, crosslinked acrylamide-sodium acrylate copolymers, gelatin, vegetable polysaccharides, such as alginates, pectins, carrageenans, or xanthan, starch and starch derivatives, galactomannan and galactomannan derivatives. polyvinyl pyrrolidone (PVP), poly(N-vinyl caprolactam) (PVCap), poly(N-vinyl acetamides), polyacrylic acid, polymethacrylic acid, and copolymers and blends thereof. PVP and PVCap. Examples of superabsorbent polymers include hydrogels. Copolymers of any of the water-vapor trapping materials mentioned herein, and blends thereof may also be used.

"Hydrophobic polymer" as used herein can refer to any polymer resistant to wetting, or not readily wet, by water, i.e., having a lack of affinity for water. Examples of hydrophobic polymers include, by way of illustration only, polyolefins, such as polyethylene, poly(isobutene), poly(isoprene), poly (4-methyl-1-pentene), polypropylene, ethylene-propylene copolymers, ethylene-propylene-hexadiene copolymers, and ethylene-vinyl acetate copolymers; metallocene polyolefins, such as ethylene-butene copolymers and ethylene-octene copolymers; styrene polymers, such as poly(styrene), poly(2-methylstyrene), and styrene-acrylonitrile copolymers having less than about 20 mole-percent acrylonitrile; vinyl polymers, such as poly(vinyl butyrate), poly(vinyl decanoate), poly(vinyl dodecanoate), poly(vinyl hexadecanoate), poly(vinyl hexanoate), poly(vinyl octanoate), and poly(methacrylonitrile); acrylic polymers, such as poly(n-butyl acetate), and poly(ethyl acrylate); methacrylic polymers, such as poly (benzyl methacrylate), poly(n-butyl methacrylate), poly (isobutyl methacrylate), poly(t-butyl methacrylate), poly(t-butylaminoethyl methacrylate), poly(do-decyl methacrylate), poly(ethyl methacrylate), poly(2-ethylhexyl methacrylate), poly(n-hexyl methacrylate), poly(phenyl methacrylate), poly(n-propyl methacrylate), and poly(octadecyl methacrylate); polyesters, such a poly(ethylene terephthalate) and poly(butylene terephthalate); and polyalkenes and polyalkynes, such as polybutylene and polyacetylene. Copolymers of any of the hydrophobic polymers mentioned herein, and blends thereof may also be used. The hydrophobic polymer also may contain minor amounts of additives as is customary in the art. For example, the hydrophobic polymer may contain pigments, delustrants, antioxidants, antistatic agents, stabilizers, oxygen scavengers, and the like. In some embodiments, the hydrophobic polymer is a polymer having a bulk density of at least about 1.00 grams per cubic centimeter (g/cc). In some embodiments, the hydrophobic polymer is a polymer having a bulk density of greater than about 1.00 gram per cubic centimeter (g/cc). In some embodiments, the hydrophobic polymer is a polymer having a bulk density of one of at least about 1.01, 1.02, 1.03, 1.05, 1.06, 1.07, 1.08, 1.09, 2.00, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40 grams per cubic centimeter (g/cc). In referring to bulk density, "about" refers to variations of 0.001 to 0.005, or of 0.005 to 0.01 grams per cubic centimeter (g/cc).

"Polyolefin" as used herein can refer to a polymer prepared by the addition polymerization of one or more unsaturated monomers which contain only carbon and hydrogen atoms. Examples of such polyolefins include polyethylene, polypropylene, poly(1-butene), poly(2-butene), poly(1-pentene), poly(2-pentene), poly(3-methyl-1-pentene), poly(4-methyl-1-pentene), and the like. In addition, such term is meant to include blends of two or more polyolefins and random and block copolymers prepared from two or more different unsaturated monomers.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfluoropropane, chloroform, trichloro-fluoromethane, dichloro-difluoromethane, dichloro-tetrafluoroethane), 1,1,1,2,3,3-hexafluoropropane (R236ea) and mixtures thereof.

"Sintering" as used herein refers to the process by which the co-deposited impermeable dispersed solid-polymer matrix, as described herein, or the hydrophobic polymer and water-vapor-trapping material becomes fused and adherent to the substrate by treatment of the coated substrate with a compressed gas, compressed liquid, or supercritical fluid that is a non-solvent for both the polymer and the impermeable dispersed solid or the hydrophobic polymer and water-vapor-trapping material, but a plasticizing agent for the polymer(s).

"Rapid Expansion of Supercritical Solutions" or "RESS" as used herein involves the dissolution of a polymer into a compressed fluid, typically supercritical $CO_2$, followed by rapid expansion into a chamber at atmospheric pressure. The rapid expansion of the supercritical fluid solution through a small opening, with its accompanying decrease in density, reduces the dissolution capacity of the fluid and results in the nucleation and growth of polymer particles.

"Solution Enhanced Dispersion of Supercritical Solutions" or "SEDS" as used herein involves a spray process for the generation of polymer particles, which are formed when a compressed fluid (e.g. supercritical fluid, preferably supercritical $CO_2$) is used as a diluent to a vehicle in which a polymer dissolved, (one that can dissolve both the polymer and the compressed gas). The mixing of the compressed fluid diluent with the polymer-containing solution may be achieved by encounter of a first stream containing the polymer solution and a second stream containing the diluent compressed fluid, for example, within one spray nozzle or by the use of multiple spray nozzles. The solvent in the polymer solution may be one compound or a mixture of two or more ingredients and may be or comprise an alcohol (including diols, triols, etc.), ether, amine, ketone, carbonate, or alkanes, or hydrocarbon (aliphatic or aromatic) or may be a mixture of compounds, such as mixtures of alkanes, or mixtures of one or more alkanes in combination with additional compounds such as one or more alcohols. (e.g., from 0 or 0.1 to 5% of a $C_1$ to $C_{15}$ alcohol, including diols, triols, etc.). See for example U.S. Pat. No. 6,669,785. The solvent may optionally contain a surfactant, as also described in (for example) U.S. Pat. No. 6,669,785.

In one embodiment of the SEDS process, a first stream of fluid comprising a polymer dissolved in a common solvent is co-sprayed with a second stream of compressed fluid. Polymer particles are produced as the second stream acts as a diluent that weakens the solvent in the polymer solution of the first stream. The now combined streams of fluid, along with the polymer particles, flow out of the nozzle assembly into a collection vessel. Control of particle size, particle size distribution, and morphology is achieved by tailoring the following process variables: temperature, pressure, solvent composition of the first stream, flow-rate of the first stream, flow-rate of the second stream, composition of the second stream (where soluble additives may be added to the compressed gas), and conditions of the capture vessel. Typically the capture vessel contains a fluid phase that is at least five to ten times (5-10×) atmospheric pressure.

"Electrostatically charged" or "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the fluid medium of the capture vessel onto the surface of the substrate is enhanced via electrostatic attraction. This may be achieved by charging the particles and grounding the substrate or conversely charging the substrate and grounding the particles, or by some other process, which would be easily envisaged by one of skill in the art of electrostatic capture.

"Electrostatic Rapid Expansion of Supercritical Solutions" or "e-RESS" or "eRESS" as used herein refers to Electrostatic Capture as described herein combined with Rapid Expansion of Supercritical Solutions as described herein.

"Electrostatic Solution Enhanced Dispersion of Supercritical Solutions" or "e-SEDS" or "eSEDS" as used herein refers to Electrostatic Capture as described herein combined with Solution Enhanced Dispersion of Supercritical Solutions as described herein.

"Electrostatic Dry Powder Coating" or "e-DPC" or "eDPC" as used herein refers to Electrostatic Capture as described herein combined with Dry Powder Coating. e-DPC deposits material (including, for example, polymer or impermeable dispersed solid) on the device or other substrate as dry powder, using electrostatic capture to attract the powder particles to the substrate. Dry powder spraying ("Dry Powder Coating" or "DPC") is well known in the art, and dry powder spraying coupled with electrostatic capture has been described, for example in U.S. Pat. Nos. 5,470,603; 6,319,541; or 6,372,246.

"Open vessel" as used herein refers to a vessel open to the outside atmosphere, and thus at substantially the same temperature and pressure as the outside atmosphere.

"Closed vessel" as used herein refers to a vessel sealed from the outside atmosphere, and thus may be at significantly different temperatures and pressures to the outside atmosphere.

EXAMPLES

The following examples are given to enable those skilled in the art to more clearly understand and to practice the present invention. They should not be considered as limiting the scope of the invention, but merely as being illustrative and representative thereof.

Example 1

A biocompatible fluoropolymer or other hydrophobic biocompatible polymer is dissolved in an appropriate supercritical solvent such as carbon dioxide. This solution is maintained in a syringe pump or other pressure vessel and transferred to a spraying vessel that is maintained above the compressed gas's critical pressure and temperature as modified by the solute. The device or other substrate to be coated is held such that it can placed at an electrical potential relative to a nozzle through which the compressed gas solution is to be sprayed (10 kV, for example, with the device held at 5 kV and the nozzle held at −5 kV). The electrical field between the device and the nozzle is designed to be homogenous and constant. The polymer solution is expanded through the restrictor nozzle by electrostatic rapid expansion of a supercritical solution (e-RESS), thereby coating the device with a fine film controllable in both thickness and conformality. Subsequent processing in the gas in its uncompressed state further reduces the volume of the film increasing its conformality. A second layer is deposited consisting of a silicon based polymer in the same manner as the first polymer layer. Alternatively, this polymer could be deposited as a dry dispersed solid using e-DPC or from solution in a compressed gas solvent. This silicon based polymer is selected so that it traps any water vapor that permeates the fluoropolymer layer. Finally, the polymer stack is completed by deposition of another layer of fluoropolymer using the e-RESS process and processed to reduce its volume (processing in the gas in its uncompressed state to further reduce the volume of the film and increase its conformality).

Example 2

A biocompatible fluoropolymer or other hydrophobic biocompatible polymer is dissolved in an appropriate supercritical solvent such as carbon dioxide. This solution is maintained in a syringe pump or other pressure vessel and transferred to a spraying vessel that is maintained above the compressed gas's critical pressure and temperature as modified by the solute. The device or other substrate to be coated is held such that it can placed at an electrical potential relative to a nozzle through which the compressed gas solution is to be sprayed (10 kV, for example, with the device held at 5 kV and the nozzle held at −5 kV). The electrical field between the device and the nozzle is designed to be homogenous and constant. The polymer solution is expanded through the restrictor nozzle by electrostatic rapid expansion of a supercritical solution (e-RESS), thereby coating the device with a fine film controllable in both thickness and conformality. Subsequent processing in the gas in its uncompressed state further reduces the volume of the film increasing its conformality. A second layer of carbonaceous material is deposited by e-DPC. A quantity of carbonaceous material is loaded as a plug into a chamber. The quantity of material initially loaded is dependent upon the desired coating mass and is a function of the potential at which the device or other substrate is held and the backpressure placed on the plug. A valve is rapidly opened through which the material expands creating an aerosolized cloud which coats the device or other substrate as a dry powder. This coating is immediately followed with a second fluoropolymer coating and undergoes the same volume reducing process as the initial layer (processing in the gas in its uncompressed state to further reduce the volume of the film and increase its conformality).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following Claims define the scope of the invention and that methods and structures within the scope of these Claims and their equivalents be covered thereby.

What is claimed is:

1. A method of preparing a coated biomedical implant comprising:
   providing a biomedical implant;
   depositing on said biomedical implant a first layer comprising a hydrophobic polymer;
   depositing on said biomedical implant a second layer comprising an impermeable dispersed solid, wherein the impermeable dispersed solid and the hydrophobic polymer are discharged separately through a first and/or second orifice and wherein the impermeable solid is discharged through the first or second orifice as a dry powder and deposited in dry powder form, and
   sintering the first and second layers under conditions that do not substantially disrupt the activity and/or function of the biomedical implant thereby forming a coating,
   wherein the coating substantially seals the biomedical implant; and
   wherein the coating is substantially impermeable to a gas; the coating is substantially impermeable to a fluid; and the coating is substantially impervious to a biological material.

2. The method of claim 1, wherein the polymer is at least one of a polyolefin, a metallocene polyolefin, a styrene polymer, a vinyl polymer, an acrylic polymer, a polyester, a polyalkene, and a polyalkyne.

3. The method of claim 1, wherein the polymer has a bulk density of at least about one of 1.01, 1.02, 1.03, 1.05, 1.06, 1.07, 1.08, 1.09, 2.00, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, and 2.40 grams per cubic centimeter (g/cc).

4. The method of claim 1, wherein the impermeable dispersed solid is impermeable to a gas.

5. The method of claim 4, wherein at least one of the polymer and the impermeable dispersed solid is electrostatically deposited onto the biomedical implant, wherein the polymer initially forms individual polymer nanoparticles that subsequently coalesce with adjacent polymer nanoparticles to form the coating.

6. The method of claim 1, comprising depositing 5, 10, 20, 50, or 100 layers of the polymer and the impermeable dispersed solid.

7. The method of claim 1, wherein depositing said impermeable dispersed solid provides improved adherence of the impermeable dispersed solid to at least one of the biomedical implant and the hydrophobic polymer.

8. The method of claim 1, wherein the oxygen transmission rate across the coating is at most about 1%, 5%, 10%, 20%, 30%, 40%, 50%, 60%, or 70%.

9. The method of claim 1 wherein the water vapor permeation through the coating is at most about 1%, 5%, 10%, 20%, 30%, 40%, 50%, 60%, or 70%.

10. The method of claim 1 wherein the small particle transmission rate across the coating is at most about 0.001%, 0.01%, 0.1%, 1%, 5%, 10%, 20%, 30%, 40%, 50%, 60%, or 70%.

11. The method of claim 1, wherein said biomedical implant is selected from the group consisting of a stent, electrode, catheter, lead, implantable pacemaker, implantable cardioverter, a housing for an implantable pacemaker, a housing for an implantable defibrillator, a housing for an implantable cardioverter, sensor, drug delivery device, therapy delivery device, device comprising telemetry capability, device comprising electrical impulses, diagnostic device, measurement device, joint, screw, rod, ophthalmic implant, femoral pin, bone plate, graft, anastomotic device, perivascular wrap, suture, staple, shunts for hydrocephalus, dialysis graft, colostomy bag attachment device, ear drainage tube, lead for pace makers and implantable cardioverters and defibrillators, vertebral disk, bone pin, suture anchor, hemostatic barrier, clamp, screws, plate, clip, vascular implant, tissue adhesive, sealant, tissue scaffolds, shunts, opthalmic implant, prosthetic, shunt, urologic implant, reproductive anatomy device, gastrologic device, neurologic lead, neurologic device, various types of dressings, bone substitutes, intraluminal devices, and vascular supports.

12. The method of claim 1, wherein the coating is substantially impermeable to leachants from the biomedical implant.

13. The method of claim 1, wherein the impermeable dispersed solid comprises a nanoparticle that is impervious to small molecule transport, wherein said nanoparticle comprises ceramic, metal, clay, silica, silicon, or metal-oxide.

14. The method of claim 13, wherein said nanoparticle comprises titanium oxide.

15. The method of claim 1, wherein the impermeable dispersed solid comprises an inorganic particle of a micron or sub-micron size.

16. The method of claim 1, wherein a third layer is deposited on said biomedical implant comprising a hydrophobic polymer and the third layer is sintered under conditions that do not substantially disrupt the activity and/or function of the biomedical implant.

17. A method for depositing a coating comprising a hydrophobic polymer on a biomedical implant, comprising the following steps:
forming a coating by
  a) discharging at least one hydrophobic polymer in dry powder form through a first orifice;
  b) depositing the hydrophobic polymer onto said biomedical implant, wherein an electrical potential is maintained between the biomedical implant and the polymer particles, thereby forming said coating;
  c) discharging at least one impermeable dispersed solid in dry powder form through a second orifice;
  d) depositing the impermeable dispersed solid onto said biomedical implant, wherein an electrical potential is maintained between the biomedical implant and the impermeable dispersed solid particles; and
  e) sintering said coating under conditions that do not substantially disrupt the activity and/or function of the biomedical implant;
wherein the coating substantially seals the biomedical implant.

18. The method of claim 17, wherein the oxygen transmission rate across the coating is at most about 1%, 5%, 10%, 20%, 30%, 40%, 50%, 60%, or 70%.

19. The method of claim 17 wherein the water vapor permeation through the coating is at most about 1%, 5%, 10%, 20%, 30%, 40%, 50%, 60%, or 70%.

20. The method of claim 17 wherein the small particle transmission rate across the coating is at most about 0.001%, 0.01%, 0.1%, 1%, 5%, 10%, 20%, 30%, 40%, 50%, 60%, or 70%.

21. The method of claim 17, wherein said biomedical implant is selected from the group consisting of a stent, electrode, catheter, lead, implantable pacemaker, implantable cardioverter, a housing for an implantable pacemaker, a housing for an implantable defibrillator, a housing for an implantable cardioverter, sensor, drug delivery device, therapy delivery device, device comprising telemetry capability, device comprising electrical impulses, diagnostic device, measurement device, joint, screw, rod, ophthalmic implant, femoral pin, bone plate, graft, anastomotic device, perivascular wrap, suture, staple, shunts for hydrocephalus, dialysis graft, colostomy bag attachment device, ear drainage tube, lead for pace makers and implantable cardioverters and defibrillators, vertebral disk, bone pin, suture anchor, hemostatic barrier, clamp, screws, plate, clip, vascular implant, tissue adhesive, sealant, tissue scaffolds, shunts, opthalmic implant, prosthetic, shunt, urologic implant, reproductive anatomy device, gastrologic device, neurologic lead, neurologic device, various types of dressings, bone substitutes, intraluminal devices, and vascular supports.

22. The method of claim 17, wherein the impermeable dispersed solid is impermeable to a gas, wherein the impermeable dispersed solid is electrostatically deposited onto the biomedical implant.

23. The method of claim 22, wherein the coating comprises a microstructure; wherein the impermeable dispersed solid is sequestered within said microstructure.

24. The method of claim 17, wherein the polymer layer has a bulk density of at least about 1.00 grams per cubic centimeter (g/cc).

25. The method of claim 24, wherein the polymer has a bulk density of at least about one of 1.01, 1.02, 1.03, 1.05, 1.06, 1.07, 1.08, 1.09, 2.00, 2.01, 2.02, 2.03, 2.04, 2.05, 20.6, 20.7, 20.8, 20.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40 grams per cubic centimeter (g/cc).

* * * * *

UNITED STATES PATENT AND TRADEMARK OFFICE
CERTIFICATE OF CORRECTION

| | | |
|---|---|---|
| PATENT NO. | : 8,900,651 B2 | Page 1 of 1 |
| APPLICATION NO. | : 12/601101 | |
| DATED | : December 2, 2014 | |
| INVENTOR(S) | : McClain et al. | |

It is certified that error appears in the above-identified patent and that said Letters Patent is hereby corrected as shown below:

On the Title page, Item "(22) PCT Filed" replace "Dec. 4, 2008" with --May 23, 2008--.

Signed and Sealed this
Seventeenth Day of March, 2015

Michelle K. Lee
*Director of the United States Patent and Trademark Office*